US011883541B2

(12) United States Patent
Campochiaro et al.

(10) Patent No.: US 11,883,541 B2
(45) Date of Patent: Jan. 30, 2024

(54) NONVIRAL GENE TRANSFER TO THE SUPRACHOROIDAL SPACE

(71) Applicant: The Johns Hopkins University, Baltimore, MD (US)

(72) Inventors: Peter A. Campochiaro, Baltimore, MD (US); Jordan Green, Nottingham, MD (US); Jayoung Kim, Baltimore, MD (US); Jikui Shen, Dundalk, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 16/753,245

(22) PCT Filed: Oct. 2, 2018

(86) PCT No.: PCT/US2018/053990
§ 371 (c)(1),
(2) Date: Apr. 2, 2020

(87) PCT Pub. No.: WO2019/070727
PCT Pub. Date: Apr. 11, 2019

(65) Prior Publication Data
US 2020/0330396 A1 Oct. 22, 2020

Related U.S. Application Data

(60) Provisional application No. 62/567,043, filed on Oct. 2, 2017.

(51) Int. Cl.
*A61K 9/51* (2006.01)
*A61K 9/00* (2006.01)
*A61K 9/50* (2006.01)
A61K 45/06 (2006.01)
B82Y 5/00 (2011.01)

(52) U.S. Cl.
CPC .......... *A61K 9/5153* (2013.01); *A61K 9/0051* (2013.01); *A61K 9/5031* (2013.01); *A61K 45/06* (2013.01); *B82Y 5/00* (2013.01)

(58) Field of Classification Search
CPC ...... B82Y 5/00; A61K 9/5153; A61K 9/0051; A61K 9/5031; A61K 45/06
See application file for complete search history.

(56) References Cited

U.S. PATENT DOCUMENTS

| 8,562,966 | B2 | 10/2013 | Zugates et al. |
| 8,808,681 | B2 | 8/2014 | Anderson et al. |
| 8,992,991 | B2 | 3/2015 | Green et al. |
| 9,255,130 | B2 | 2/2016 | Yu et al. |
| 9,700,627 | B2 | 7/2017 | Langer et al. |
| 9,717,694 | B2 | 8/2017 | Green et al. |
| 2009/0011040 | A1 | 1/2009 | Naash et al. |
| 2009/0226531 | A1 | 9/2009 | Lyons et al. |
| 2012/0114759 | A1 | 5/2012 | Green et al. |
| 2012/0128782 | A1 | 5/2012 | Green et al. |
| 2012/0226260 | A1* | 9/2012 | Prausnitz ................ A61P 27/02 604/506 |
| 2015/0250881 | A1 | 9/2015 | Green et al. |
| 2015/0273071 | A1 | 10/2015 | Green et al. |
| 2016/0101054 | A1 | 4/2016 | Lavik et al. |
| 2016/0213662 | A1 | 7/2016 | Zarnitsyn et al. |
| 2016/0310417 | A1 | 10/2016 | Prausnitz et al. |
| 2016/0346359 | A1* | 12/2016 | Buchlis .............. A61K 31/7088 |
| 2016/0374949 | A9 | 12/2016 | Green et al. |

FOREIGN PATENT DOCUMENTS

| WO | WO 2010/132879 | 11/2010 | |
| WO | WO-2010132879 A2 * | 11/2010 | ........... A61K 9/1075 |
| WO | WO 2011/017313 | 2/2011 | |
| WO | WO 2016/042163 | 3/2016 | |
| WO | WO 2016/083669 | 6/2016 | |
| WO | WO 2016/154622 | 9/2016 | |

OTHER PUBLICATIONS

Thomas J. Wubben, et al, Retinal Neuroprotection: Overcoming the Translational Roadblocks, 192 Am. J Ophthalmol. 15 (Year: 2018).*
International Search Report and Written Opinion for PCT/US2018/053990, dated Apr. 30, 2019. 16 pages.
Belin et al., Recent Innovations in drug delivery for retinal diseases, Advances in Ophthalmology and Optometry, 2018, 3(1),pp. 155-183.
Belin et al., The use of bevacizumab in pediatric retinal and choroidal disease: A review. Eur J Ophthalmol. May 2019;29(3):338-347.
Bhise et al., Evaluating the potential of poly(beta-amino ester) nanoparticles for reprogramming human fibroblasts to become induced pluripotent stem cells. Int J Nanomedicine. 2013;8:4641-58.
Campochiaro et al., Enhanced Benefit in Diabetic Macular Edema from AKB-9778 Tie2 Activation Combined with Vascular Endothelial Growth Factor Suppression. Ophthalmology. Aug. 2016;123(8):1722-1730.
Campochiaro et al., Anti-Vascular Endothelial Growth Factor Agents in the Treatment of Retinal Disease: From Bench to Bedside. Ophthalmology. Oct. 2016;123(10S):S78-S88.
Campochiaro et al., Lentiviral Vector Gene Transfer of Endostatin/Angiostatin for Macular Degeneration (GEM) Study. Hum Gene Ther. Jan. 2017:28(1):99-111.
Conley et al., Nonviral ocular gene therapy: assessment and future directions. Curr Opin Mol Ther. Oct. 2008;10(5):456-63.
Green et al., A combinatorial polymer library approach yields insight into nonviral gene delivery. Acc Chem Res. Jun. 2008;41(6):749-59.
Guerrero-Cazares et al., Biodegradable polymeric nanoparticles show high efficacy and specificity at DNA delivery to human glioblastoma in vitro and in vivo. ACS Nano. May 27, 2014;8(5):5141-53.

(Continued)

*Primary Examiner* — Sean M Basquill
(74) *Attorney, Agent, or Firm* — Casimir Jones, SC; Jeffrey W. Childers

(57) ABSTRACT

The presently disclosed subject matter provides compositions and methods for administering a nanoparticle or microparticle and a therapeutic agent to the suprachoroidal space in the eye.

18 Claims, 10 Drawing Sheets

(56) References Cited

OTHER PUBLICATIONS

Heier et al., Intravitreous injection of AAV2-sFLT01 in patients with advanced neovascular age-related macular degeneration: a phase 1, open-label trial. Lancet. Jul. 1, 2017;390(10089):50-61.
Jin et al., Anti-inflammatory and antiangiogenic effects of nanoparticle-mediated delivery of a natural angiogenic inhibitor. Invest Ophthalmol Vis Sci. Aug. 5, 2011;52(9):6230-7.
Joseph et al., Recent perspectives on the delivery of biologics to back of the eye. Expert Opin Drug Deliv. May 2017;14(5):631-645.
Kawashima et al., A scalable controlled-release device for transscleral drug delivery to the retina. Biomaterials. Mar. 2011;32(7):1950-6.
Kompella et al., Nanomedicines for back of the eye drug delivery, gene delivery, and imaging. Prog Retin Eye Res. Sep. 2013;36:172-98.
Kotterman et al., Antibody neutralization poses a barrier to intravitreal adeno-associated viral vector gene delivery to non-human primates. Gene Ther. Feb. 2015;22(2):116-26.
Kumaran et al., Retinal gene therapy, Br Med Bull, (2018), 126 (1), pp. 13-25.
Kunou et al., Long-term sustained release of ganciclovir from biodegradable scleral implant for the treatment of cytomegalovirus retinitis. J Control Release. Aug. 10, 2000;68(2):263-71.
Lee et al., Efficacy and Safety of Intravitreal Aflibercept for Polypoidal Choroidal Vasculopathy in the Planet Study: A Randomized Clinical Trial. JAMA Ophthalmol. Jul. 1, 2018;136(7):786-793.
Li et al., Intraocular route of AAV2 vector administration defines humoral immune response and therapeutic potential. Mol Vis. Sep. 24, 2008;14:1760-9.
Liu et al., A lipid nanoparticle system improves siRNA efficacy in RPE cells and a laser-induced murine CNV model. Invest Ophthalmol Vis Sci. Jul. 1, 2011;52(7):4789-94.
Mangraviti et al., Polymeric nanoparticles for nonviral gene therapy extend brain tumor survival in vivo. ACS Nano. Feb. 24, 2015;9(2):1236-49.
Patel et al., Suprachoroidal drug delivery to the back of the eye using hollow microneedles. Pharm Res. Jan. 2011;28(1):166-76.
Patel et al., Targeted administration into the suprachoroidal space using a microneedle for drug delivery to the posterior segment of the eye. Invest Ophthalmol Vis Sci. Jul. 1, 2012;53(8):4433-41.
Pescina et al., Therapeutics and carriers: the dual role of proteins in nanoparticles for ocular delivery. Curr Top Med Chem. 2015:15(4):369-85.
Recchia. AAV-CRISPR Persistence in the Eye of the Beholder. Mol Ther. Jan. 2, 2019;27(1):12-14.
Shen et al., Targeting VE-PTP activates TIE2 and stabilizes the ocular vasculature. J Clin Invest. Oct. 2014;124(10):4564-76.
Shmueli et al., Long-term suppression of ocular neovascularization by intraocular injection of biodegradable polymeric particles containing a serpin-derived peptide. Biomaterials. Oct. 2013;34(30):7544-51.
Sousa et al., Nanoparticles for the delivery of therapeutic antibodies: Dogma or promising strategy? Expert Opin Drug Deliv. Oct. 2017;14(10):1163-1176.
Sunshine et al., Small-Molecule End-Groups of Linear Polymer Determine Cell-type Gene-Delivery Efficacy. Adv Mater. Dec. 28, 2009;21(48):4947-4951.
Sunshine et al., Poly(β-amino ester)-nanoparticle mediated transfection of retinal pigment epithelial cells in vitro and in vivo. PLoS One. 2012;7(5):e37543. 11 pages.
Touchard et al., Suprachoroidal electrotransfer: a nonviral gene delivery method to transfect the choroid and the retina without detaching the retina. Mol Ther. Aug. 2012;20(8):1559-70.
Vandenberghe et al., Dosage thresholds for AAV2 and AAV8 photoreceptor gene therapy in monkey. Sci Transl Med. Jun. 22, 2011;3(88):88ra54. 20 pages.
Zarbin et al., Vascular Safety of Ranibizumab in Patients With Diabetic Macular Edema: A Pooled Analysis of Patient-Level Data From Randomized Clinical Trials. JAMA Ophthalmol. May 1, 2017;135(5):424-431.

\* cited by examiner

NONVIRAL GENE TRANSFER TO THE SUPRACHOROIDAL SPACE

CROSS-REFERENCE TO RELATED APPLICATIONS

This application is a U.S. National Entry Application of PCT/US2018/053990, filed Oct. 2, 2018, which claims the benefit of U.S. Provisional Application No. 62/567,043, filed Oct. 2, 2017, each of which is incorporated herein by reference in its entirety.

FEDERALLY SPONSORED RESEARCH OR DEVELOPMENT

This invention was made with government support under EB016721 and EY022986 awarded by the National Institutes of Health. The government has certain rights in the invention.

BACKGROUND

Ocular gene transfer provides a means of sustained delivery of proteins and peptides to the eye. Gene transfer with adeno-associated viral (AAV) or lentiviral vectors can provide long-term expression in cells that have appropriate receptors for transduction. Viral vectors, however, can induce an immune response, which makes repeated administration improbable. Viral vectors also have limitations in cargo capacity. An alternative to viral vectors for ocular gene transfer is nonviral gene transfer with biodegradable particles. Transfection efficiency with nonviral gene transfer, however, is generally substantially less compared to that with viral vectors.

SUMMARY

In some aspects, the presently disclosed subject matter provides for a method of treating a subject with a disease or condition of the eye, comprising administering to the suprachoroidal space a composition comprising a nanoparticle or microparticle and a therapeutic agent. As used herein, the suprachoroidal space refers to the area between the sclera and the choroid. This area may be expanded upon administration of a composition. In certain aspects, the nanoparticle or microparticle may comprise a poly(beta-amino ester) (PBAE), or a polyethylene glycol-b-poly(beta-amino ester) (PEG-PBAE) co-polymer. In other aspects, the PBAE may comprise a compound of formula (I):

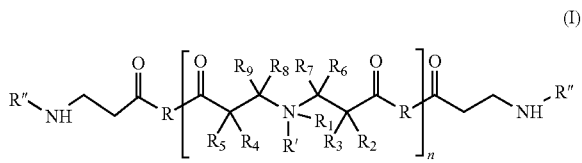

In other aspects, the PBAE may comprise a compound of formula (I) or formula (II):

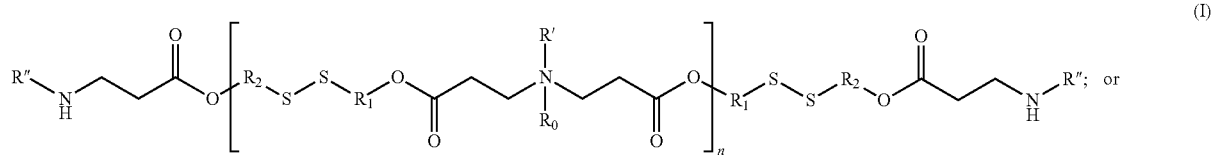

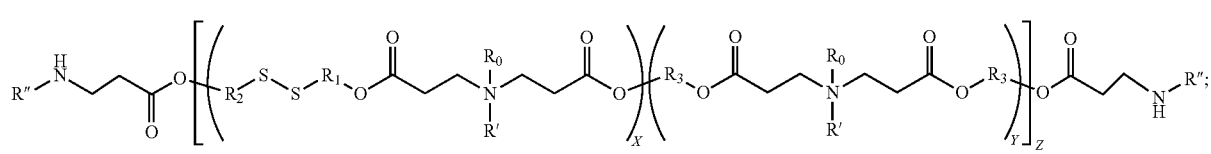

In yet another aspect, the PBAE may comprise a compound of formula (I):

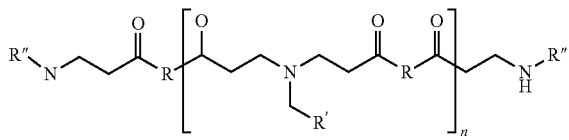

In some aspects, the PEG-PBAE may be PEG0.8k-B4S44k-PEG0.8k, PEG0.8k-B4S413k-PEG0.8k, PEG5k-B4S44k-PEG5k, or PEG5k-B4S413k-PEG5k.

In another aspect, the nanoparticle or the microparticle may be formulated to spread after delivery to the suprachoroidal space and uniformly distribute and localize in a region of the suprachoroidal space, and wherein the nanoparticle or the microparticle localizes to a cell type. The composition may further comprise a pharmaceutically acceptable carrier.

In some aspects, the therapeutic agent may be a drug, small molecule, nucleic acid sequence, amino acid sequence, gene, transgene, peptide, protein, expression vector, carbohydrate, lipid, sugar, antibody or antibody fragment thereof, hormone, hormone receptor, receptor ligand, or cancer cell specific ligand.

In some aspects, the therapeutic agent may neutralize the activity of a protein in the eye. In another aspect, the therapeutic agent may neutralize the activity of a growth factor. In another aspect, the therapeutic agent may stimulate the activity of a growth factor. In other aspects, the therapeutic agent may neutralize or stimulate the activity of at least one of vascular endothelial growth factor (VEGF), platelet-derived growth factor (PDGF), angiopoietin 2 (Angpt2), vascular endothelial-protein tyrosine phosphate (VE-PTP), or combinations thereof.

In another aspect, the nanoparticle or the microparticle may localize to at least one specific cell type in the eye. In some aspects, the at least one cell type may be a retinal ganglion cell, amacrine cell, Müller cell, astrocyte, photoreceptor cell, cone cell, rod cell, bipolar cell, horizontal cell, retinal pigment epithelial cell, choroidal cell, or a scleral cell.

In another aspect, the disease or condition may be age-related macular degeneration (AMD), neovascular age-related macular degeneration (NVAMD), retinitis pigmentosa (RP), optic neuritis, infection, uveitis, sarcoid, sickle cell disease, retinal detachment, temporal arteritis, retinal ischemia, choroidal ischemia, choroidal ischemia, ischemic optic neuropathy, arteriosclerotic retinopathy, hypertensive retinopathy, retinal artery blockage, retinal vein blockage, glaucoma, hypotension, diabetic retinopathy, diabetic macular edema (DME), macular edema occurring after retinal vein occlusion (RVO), macular edema, and choroidal neovascularization.

In yet other aspects, the disease or condition is an inherited retinal degeneration. In such aspects, the therapeutic agent comprises a gene associated with inherited retinal degenerations. In particular aspects, the nanoparticle or microparticle encapsulates a plasmid that encodes a gene that replaces defective genes due to inherited retinal diseases, wherein the gene is selected from the group consisting of RPE65, BEST1, NR2E3, NRL, RHO, RP1, an autosomal dominant, an autosomal recessive gene, and an X-linked gene. In yet more particular aspects, the X-linked gene is selected from the group consisting of RPGR, RP2, and OFD1. In certain aspects, the disease or condition is selected from the group consisting of Stargardt disease, choroideremia, achromatopsia, and X-linked retinitis pigmentosa.

In other aspects, the disease or condition includes cone cell death in patients with retinitis pigmentosa. In such aspects, the therapeutic agent comprises a therapeutic protein for preventing cone cell death in patients with retinitis pigmentosa. In particular aspects, the nanoparticle or microparticle encapsulates a plasmid that encodes NRF2, GDNF, or another gene that is neuroprotective to the retina.

In another aspect, the composition may be administered at least twice, wherein each administration is done at a different time point. In another aspect, the composition may be administered at a dosage of about 0.0001 mg/kg to about 5 mg/kg.

In some aspects, the disclosed subject matter provides for a method of delivering a composition to the suprachoroidal space of the eye, the method comprising: (a) preparing a composition comprising a pharmaceutically acceptable carrier and a nanoparticle or a microparticle, wherein the nanoparticle or microparticle comprises a therapeutic agent; and (b) administering the composition to the suprachoroidal space of the eye, wherein the nanoparticle is targeted to a cell in the eye.

In another aspect, the disclosed subject matter provides for a kit, which may comprise: (a) a reagent comprising a nanoparticle and a therapeutic agent; and (b) instructions for using the pharmaceutical composition.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
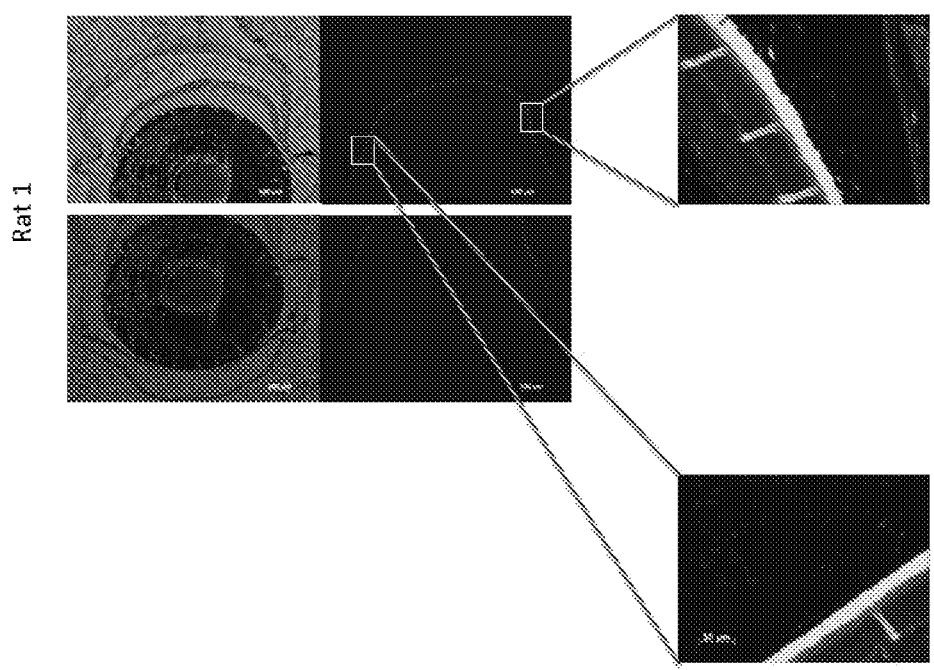
Figure 2:
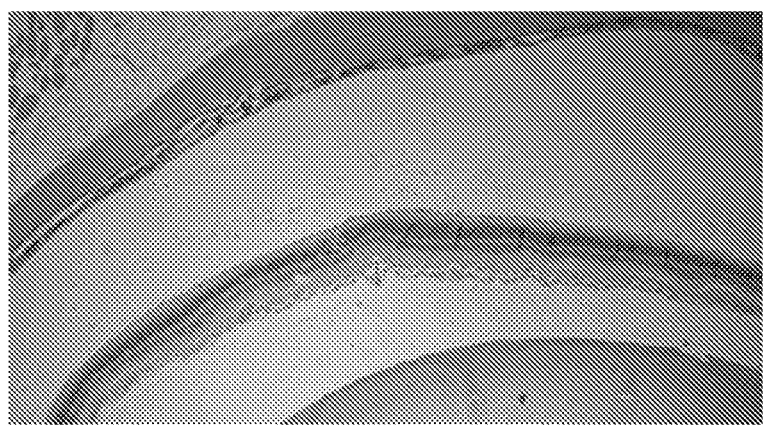
Figure 3:
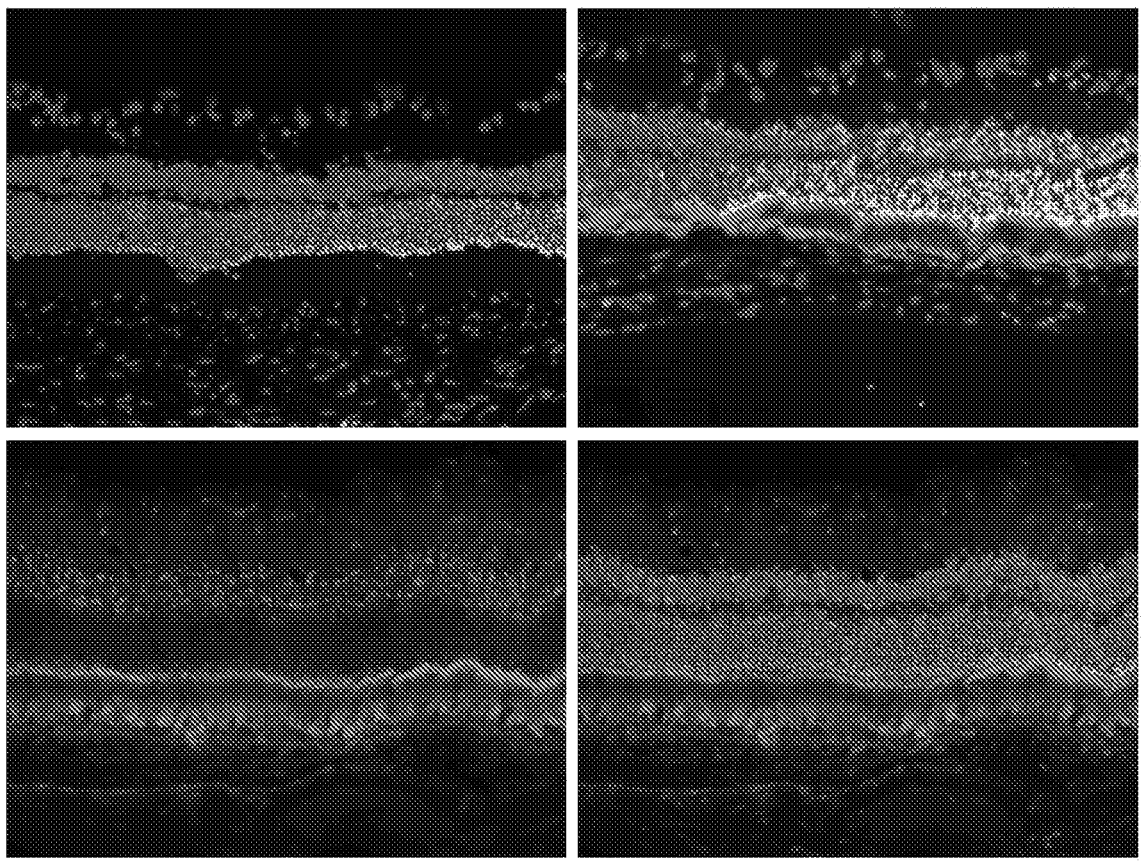
Figure 4:
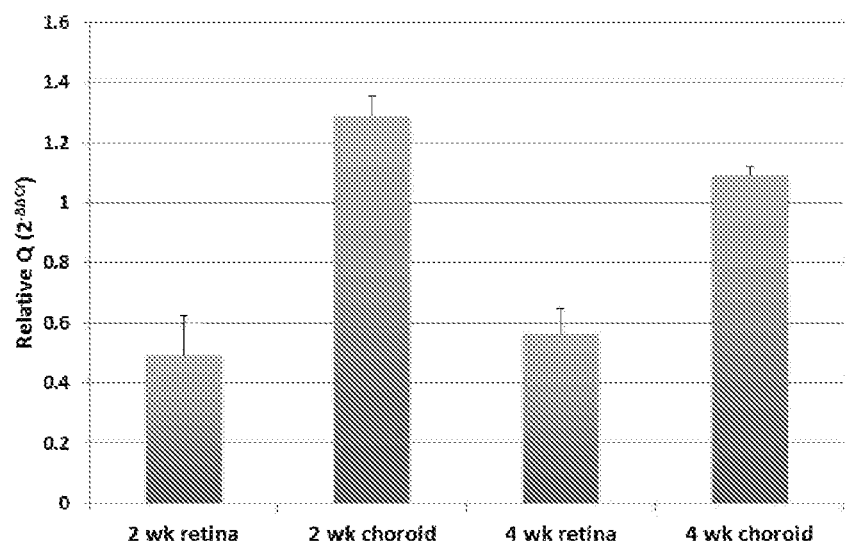
Figure 5:
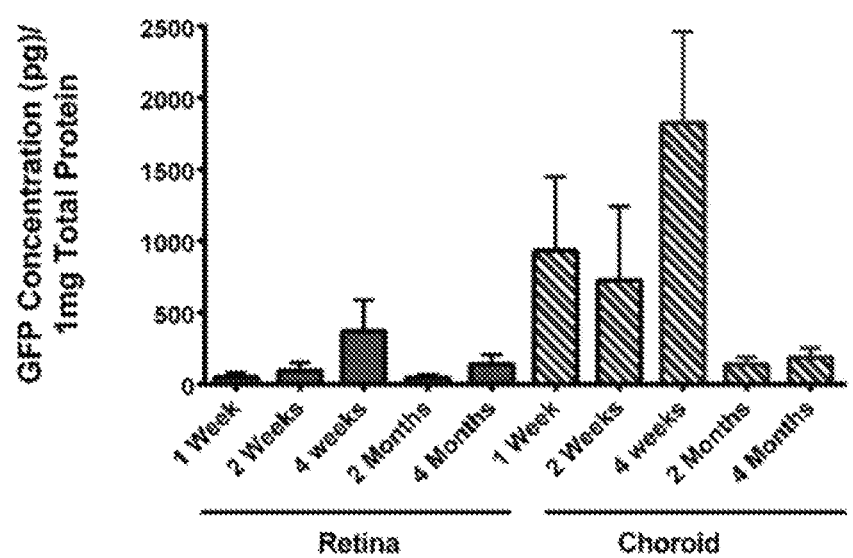
Figure 6A:
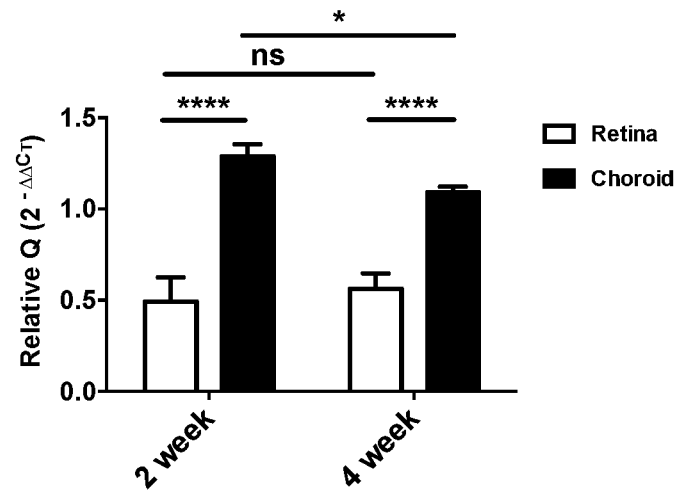
Figure 6B:
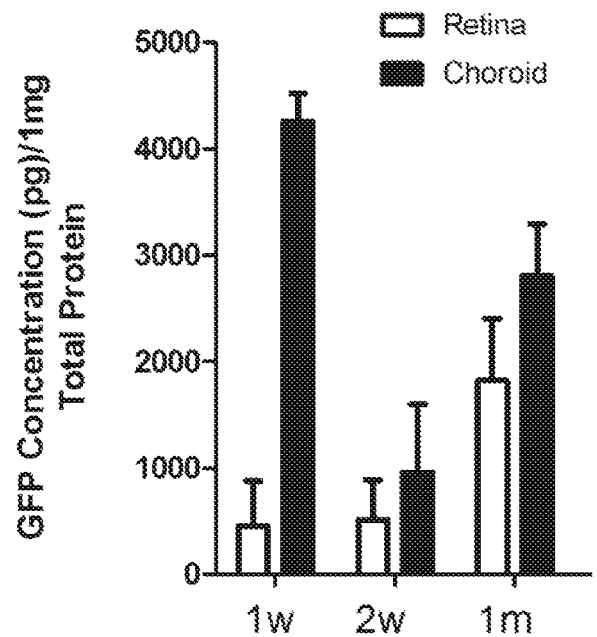
Figure 6C:
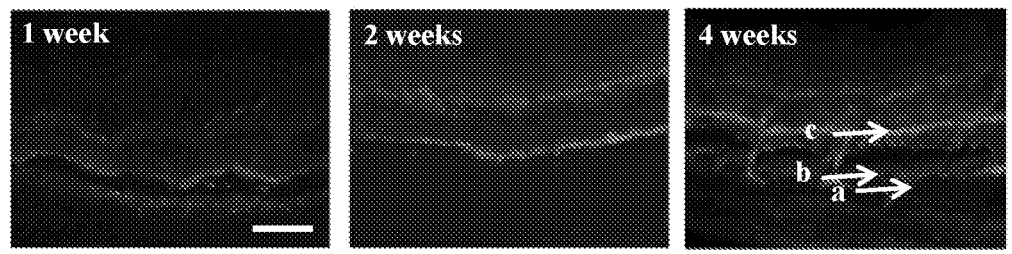
Figure 6D:
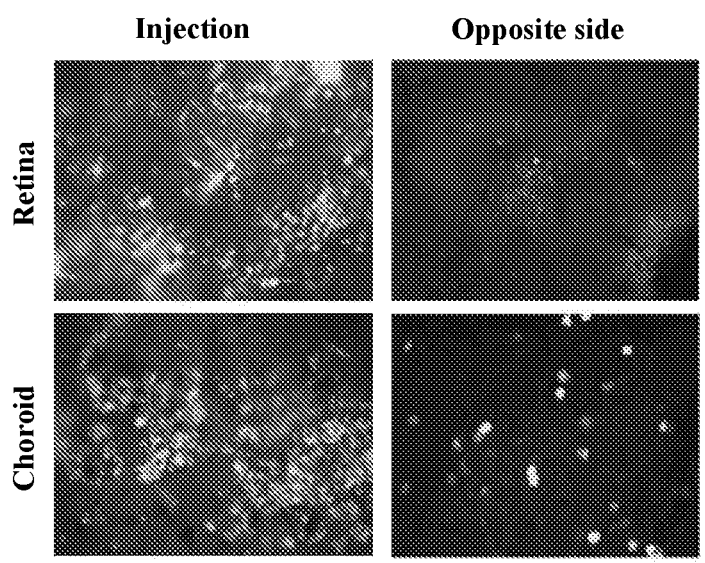
Figure 7:
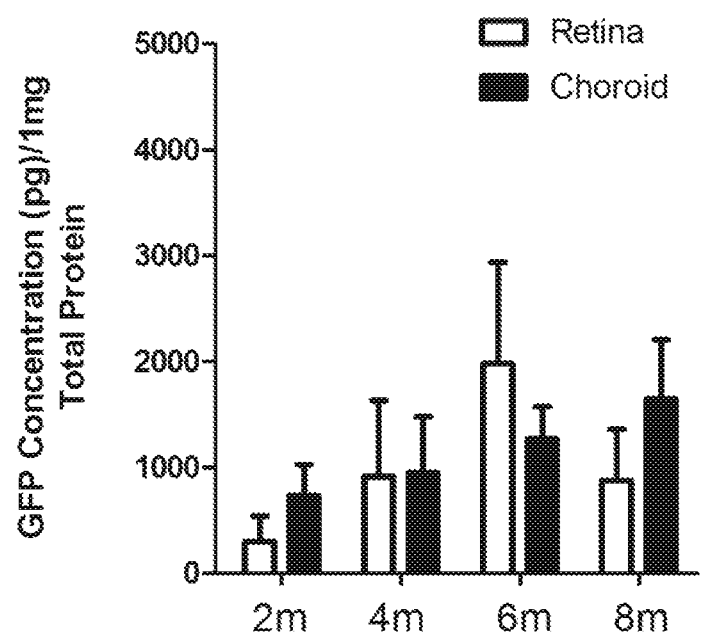
Figure 8:
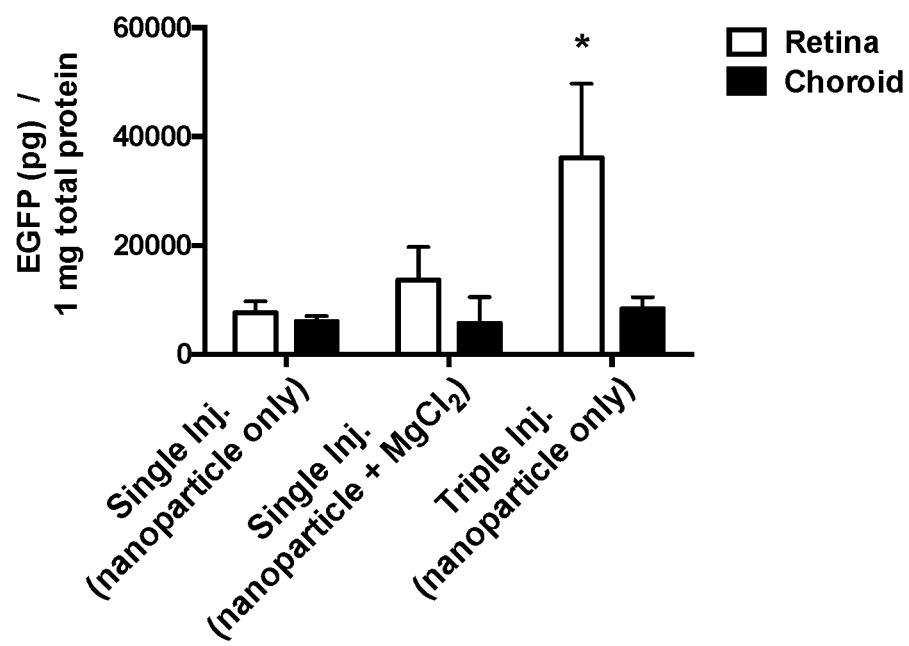
Figure 9A:
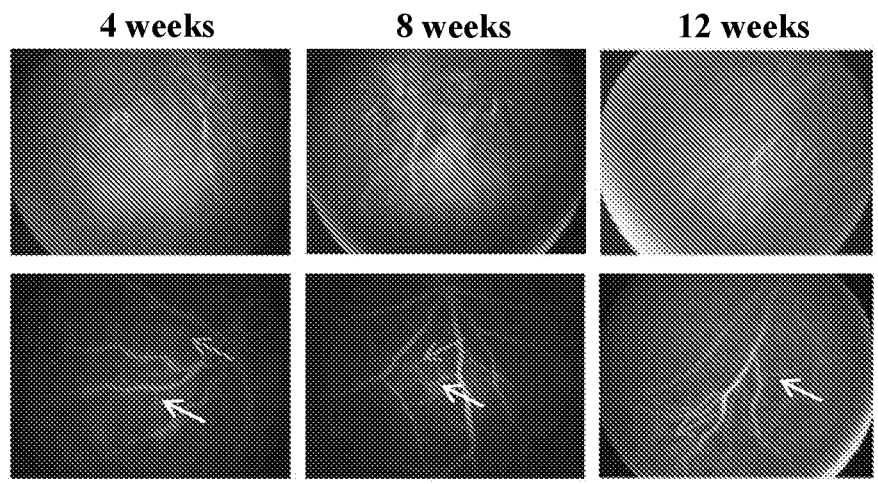
Figure 9B:
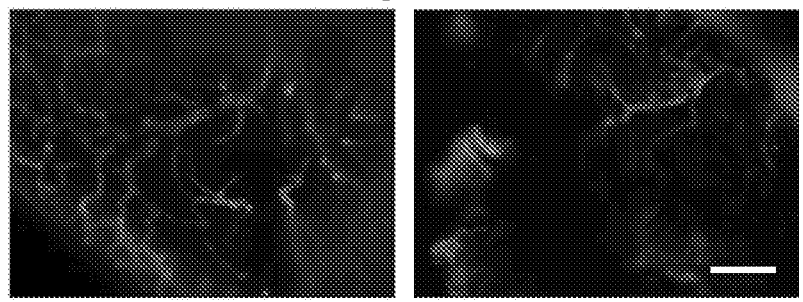
Figure 9C:
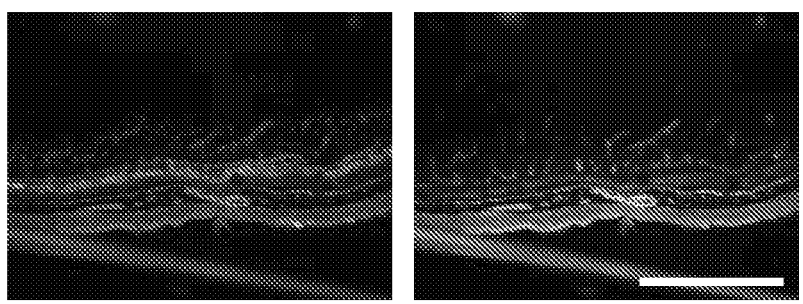

Having thus described the presently disclosed subject matter in general terms, reference will now be made to the accompanying Figures, which are not necessarily drawn to scale, and wherein:

FIG. 1 shows expression of green fluorescent protein (GFP) two weeks after suprachoroidal injection of a GFP expression construct packaged in representative presently disclosed nanoparticles;

FIG. 2 shows an image of an ocular section stained with hematoxylin and eosin, two weeks after suprachoroidal injection of a GFP expression construct packaged in representative presently disclosed nanoparticles, showing retinal layers for comparison with staining in FIG. 1. This comparison suggests that the GFP expression is located in the choroid, retinal pigment epithelial cells, photoreceptor inner and outer segments, and Muller cells;

FIG. 3 shows an immunofluorescent image of the distribution of green fluorescent protein (GFP) in a retinal section, two months after suprachoroidal injection;

FIG. 4 shows a bar graph of the GFP mRNA expression in retina and RPE/choroid, 2 and 4 weeks after suprachoroidal injection of a GFP expression construct packaged in polymeric nanoparticles. Expression is greater in RPE/choroid and is essentially unchanged between 2 and 4 weeks;

FIG. 5 shows a bar graph of the time course of GFP expression in the retina and RPE/choroid after suprachoroidal nonviral gene transfer;

FIG. 6A, FIG. 6B, FIG. 6C, and FIG. 6D show short-term EGFP expression following suprachoroidal injection of PBAE-pEGFP nanoparticle. FIG. 6A shows qRT-PCR of EGFP mRNA level in retina and choroid at 2 and 4 weeks post injection (n=4, mean±SD, One-way ANOVA with Tukey post-hoc test); FIG. 6B is ELISA of EGFP protein level in retina and choroid at 1, 2, and 4 weeks post injection (n=3 for 1 week, n=7 for 2 weeks, n=8 for 4 weeks, mean±SEM); FIG. 6C shows ocular sections immunostained with EGFP antibody (a: suprachoroidal space, b: RPE/choroid, c: inner segment, scale bar=25 μm); and FIG. 6D shows whole mount images showing EGFP fluorescence (scale bar=50 μm);

FIG. 7 shows long-term EGFP expression following suprachoroidal injection of PBAE-pEGFP nanoparticle. ELISA measurement of EGFP protein expression level at 2, 4, 6, and 8 months following suprachoroidal injection of PBAE-pEGFP nanoparticles (n≥5, mean±SEM);

FIG. 8 is a comparison of EGFP expression level following modifications to nanoparticle injection conditions. ELISA measurement of EGFP protein expression level at 4 weeks following (the last) suprachoroidal injection of PBAE-pEGFP nanoparticles (n=10 for single injections, n≥7 for triple injections, mean±SEM, One-way ANOVA with Dunnett post-hoc test with comparison to single injection nanoparticle only control for retina and choroid); and FIG. 9A, FIG. 9B, and FIG. 9C show retinal neovascularization following suprachoroidal injection of PBAE-pVEGF nanoparticles. FIG. 9A shows fundus (top) and fluorescent angiography images visualizing IP-injected sodium fluorescein (bottom) at 4, 8, and 12 weeks post nanoparticle injection (white arrows: neovasculature, red arrows: leakage site); FIG. 9B is a fluorescence image of whole mount retinal (left) and choroidal (right) vasculature stained with GSA-lectin at 8 weeks post nanoparticle injection (scale bar=100 μm); and FIG. 9C is a fluorescent image of ocular section stained with Hoescht and GSA-lectin (left) and GSA-lectin only (right) at 16 weeks post nanoparticle injection (scale bar=100 μm).

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Nonviral Gene Transfer to the Suprachoroidal Space

Ocular gene transfer can be achieved by subretinal injection of expression constructs packaged in adeno-associated viral (AAV) vectors or lentiviral vectors. This requires an operative procedure including vitrectomy and subretinal injection of the vector, which is invasive and carries a 1% risk of retinal detachment (Campochiaro, et al., 2016). Intravitreous injection of lentiviral vectors is not feasible because of poor lentiviral infection of the cells lining the vitreous cavity. Intravitreous injection of AAV vectors results in transduction of ganglion cells only in parts of the retina where the internal limiting membrane (ILM) is thin (Vandenberghe, et al., 2011). This results in transgene expression several orders of magnitude less than that achieved with a subretinal injection of the same amount of AAV vector. Changes in vector capsids can improve transduction after intravitreous injection of AAV vectors, but it is not yet clear if expression will be sufficient for clinical application. Pre-existent serum antibodies to the AAV serotype injected into the vitreous may reduce expression, but they do not reduce expression if the AAV vector is injected into the subretinal space (Heier, et al., 2017; Li, et al., 2008; Kotterman, et al., 2014).

Suprachoroidal injections provide a new route for delivering a therapeutic agent (e.g., a drug, a biologically active agent) to the suprachoroid space (Patel, et al., 2011; Patel, et al., 2012). The suprachoroidal space may expand when fluid is injected just internal to the sclera, providing an advantage over intravitreous injections for some drugs because they may increase delivery to the retina and minimize delivery to anterior structures of the eye.

Nonviral gene transfer with biodegradable particles is an alternative to viral vectors for ocular gene transfer. Transfection efficiency with nonviral gene transfer, however, is generally substantially less compared to that with viral vectors. The presently disclosed subject matter overcomes this problem by providing a method for injecting nanoparticle- or microparticle-containing expression constructs into the suprachoroidal space. Because the suprachoroidal space is expanded by the injection, cells and particles are kept in close proximity. This characteristic, in addition to the nature of the cells in the suprachoroid, results in good transfection and sustained expression after suprachoroidal injection of the particles. Further, suprachoroidal injections are relatively noninvasive and can be done in an outpatient clinic setting making repeated injections feasible. Thus, the presently disclosed subject matter provides a method for the sustained delivery of, for example, proteins and peptides, to the retina and choroid.

Previous efforts have compacted expression plasmids with poly(beta-amino ester)s (PBAEs) to form biodegradable nanoparticles that provide efficient gene transfer to glioblastoma cells or retinal pigmented epithelial (RPE) cells in vitro or in vivo (Green, et al., 2008; Sunshine, et al., 2009; Sunshine, et al., 2012; Guerrero-Cazares, et al., 2014; Mangraviti, et al., 2015).

Poly(beta-amino ester)s (PBAEs) suitable for use with the presently disclosed methods are disclosed in:

International PCT patent application publication no. WO2010/132879 for Multicomponent Degradable Cationic Polymers to Green et al., published Nov. 18, 2010;

U.S. patent application publication no. 20120128782 for Multicomponent Degradable Cationic Polymers, to Green et al., published May 24, 2012;

U.S. patent application publication no. 20120114759 and 20160374949 for Peptide/particle Delivery Systems, to Green et al., published May 10, 2012, and Dec. 29, 2016, respectively;

U.S. patent application publication no. 20150250881 for Multicomponent Degradable Cationic Polymers, to Green et al., published Sep. 10, 2015;

U.S. patent application publication no. 20150273071 for Bioreducible Poly (Beta-Amino Ester)s For siRNA Delivery, to Green et al., published Oct. 1, 2015;

International PCT patent application publication no. WO2016/154622 for Poly(Beta-Amino Ester)-Co-Polyethylene Glycol (PEG-PBAE-PEG) Polymers For Gene And Drug Delivery, to Green et al., published Sep. 29, 2016;

U.S. Pat. No. 8,992,991 for Multicomponent Degradable Cationic Polymers, to Green et al., issued Mar. 31, 2015; and U.S. Pat. No. 9,717,694 for Peptide/particle delivery systems to Green et al., issued Aug. 1, 2017; each of which is incorporated herein by reference in their entirety.

A. Representative Bioreducible Poly(Beta-Amino Ester)s (PBAEs)

In some embodiments, the bioreducible (biodegradable) nanoparticle or microparticle suitable for use with the presently disclosed methods comprises a PBAE of formula (I) as disclosed in international PCT patent application publication no. WO2010/132879 or U.S. patent application publication no. 20120128782:

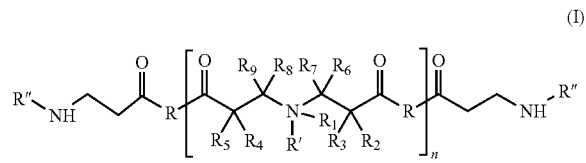

(I)

wherein:

n is an integer from 1 to 10,000;

$R_1$, $R_2$, $R_3$, $R_4$, $R_5$, $R_6$, $R_7$, $R_8$, and $R_9$ are each independently selected from the group consisting of hydrogen, branched and unbranched alkyl, branched and unbranched alkenyl, branched and unbranched alkynyl, aryl, halogen, hydroxyl, alkoxy, carbamoyl, carboxyl ester, carbonyldioxyl, amide, thiohydroxyl, alkylthioether, amino, alkylamino, dialkylamino, trialkylamino, cyano, ureido, a substituted alkanoyl group, cyclic, cyclic aromatic, heterocyclic, and aromatic heterocyclic groups, each of which may be substituted with at least one substituent selected from the group consisting of branched or unbranched alkyl, branched and unbranched alkenyl, branched and unbranched alkynyl, amino, alkylamino, dialkylamino, trialkylamino, aryl, ureido, heterocyclic, aromatic heterocyclic, cyclic, aromatic cyclic, halogen, hydroxyl, alkoxy, cyano, amide, carbamoyl, carboxylic acid, ester, carbonyl, carbonyldioxyl, alkylthioether, and thiohydroxyl groups;

wherein $R_1$ can be present or absent and when present the compound of formula (I) further comprises a counter ion selected from the group consisting of chloride, fluoride, bromide, iodide, sulfate, nitrate, fumarate, acetate, carbonate, stearate, laurate, and oleate; and at least one of R, R', and R" comprise a reducible or degradable linkage, and wherein each R, R', or R" can independently be the same or different;

under the proviso that when at least one R group comprises an ester linkage of the formula —C(=O)—O— and the compound of formula (I) comprises a poly (beta-amino ester), then the compound of formula (I) must also comprise one or more of the following characteristics:

(a) each R group is different;
(b) each R" group is different;
(c) each R" group is not the same as any of R', $R_1$, $R_2$, $R_3$, $R_4$, $R_5$, $R_6$, $R_7$, $R_8$, and $R_9$;
(d) the R" groups degrade through a different mechanism than the ester-containing R groups, wherein the degradation of the R" group is selected from the group consisting of a bioreducible mechanism or an enzymatically degradable mechanism; and/or
(e) the compound of formula (I) comprises a substructure of a larger cross-linked polymer, wherein the larger cross-linked polymer comprises different properties from compound of formula (I); and pharmaceutically acceptable salts thereof.

In some embodiments, the compound of formula (I) is subject to the further proviso that if at least one R group comprises an ester linkage, then the R" groups impart one or more of the following characteristics to the compound of formula (I): independent control of cell-specific uptake and/or intracellular delivery of a particle; independent control of endosomal buffering and endosomal escape; independent control of DNA release; triggered release of a therapeutic agent; modification of a particle surface charge; increased diffusion through a cytoplasm of a cell; increased active transport through a cytoplasm of a cell; increased nuclear import within a cell; increased transcription of an associated DNA within a cell; increased translation of an associated DNA within a cell; increased persistence of an associated therapeutic agent within a cell, wherein the therapeutic agent is selected from the group consisting of DNA, RNA, a peptide, or a protein.

In some embodiments, n is an integer from 1 to 1,000; in other embodiments, n is an integer from 1 to 100; in other embodiments, n is an integer from 1 to 30; in other embodiments, n is an integer from 5 to 20; in other embodiments, n is an integer from 10 to 15; and in other embodiments, n is an integer from 1 to 10.

In particular embodiments, the reducible or degradable linkage comprising R, R', and R" is selected from the group consisting of an ester, a disulfide, an amide, an anhydride or a linkage susceptible to enzymatic degradation, subject to the proviso hereinabove.

In certain embodiments, R comprises a backbone of a diacrylate selected from the group consisting of:

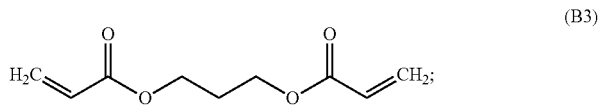

(B3)

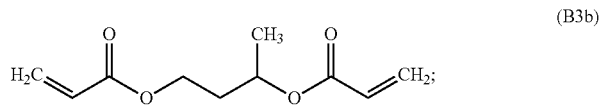

(B3b)

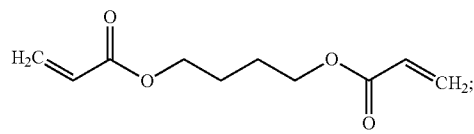 (B4)
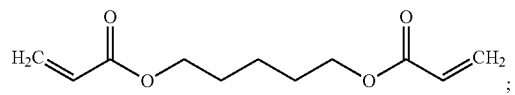 (B5)
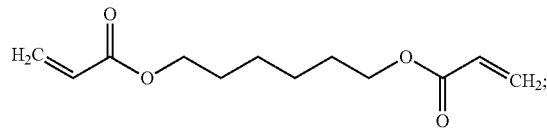 (B6)
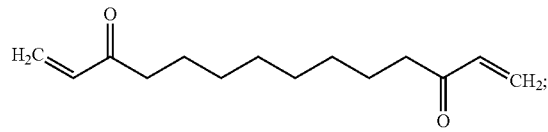 (B8)
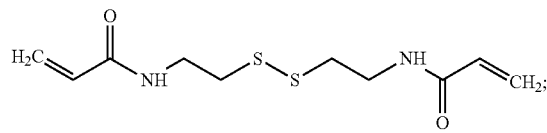 (BSS)
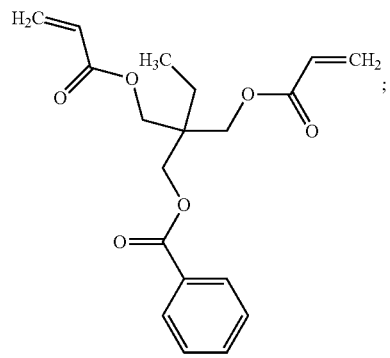 (BL1)
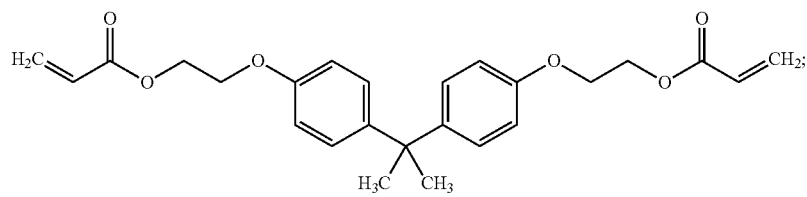 (BL2)
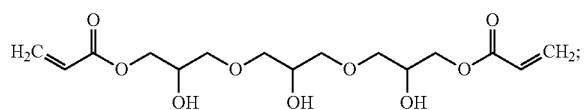 (BH1)
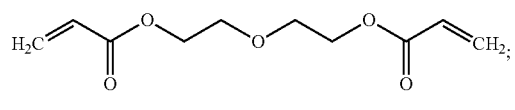 (BP1)
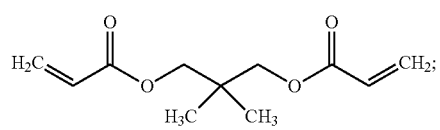 (BP2)
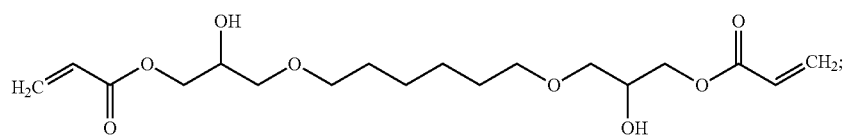 (BP3)
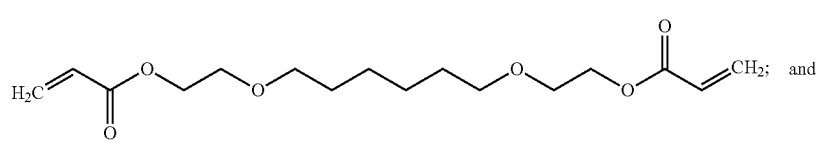 (BP4) and
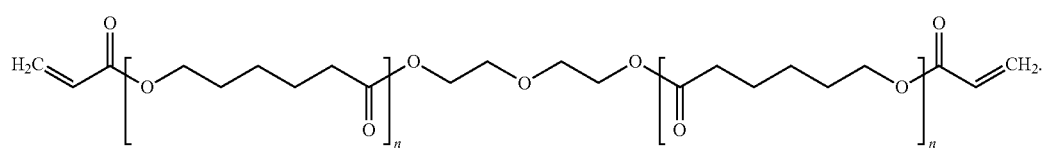 (BP6)

In some embodiments, R' is selected from the group consisting of
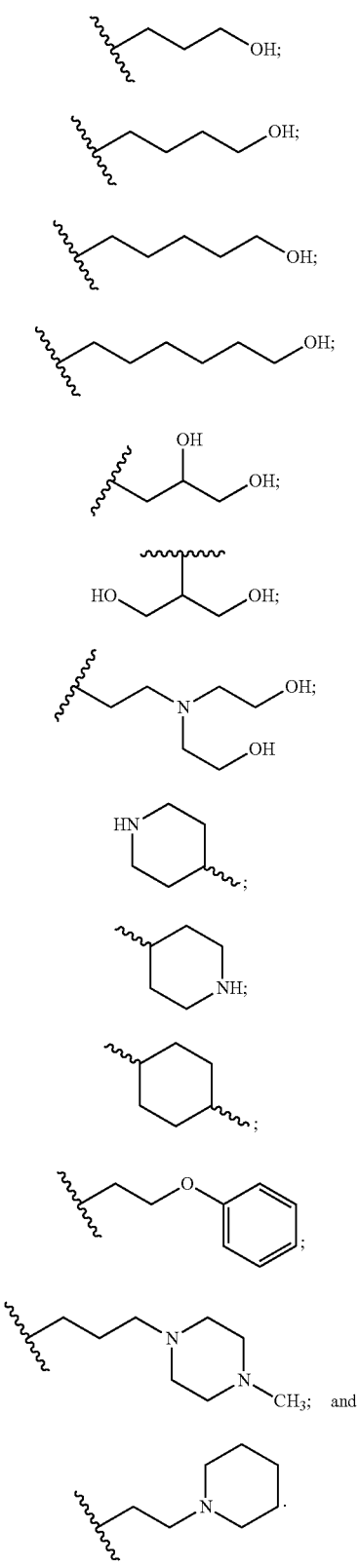
In certain embodiments, R" comprises an end group derived from a compound selected from the group consisting of:
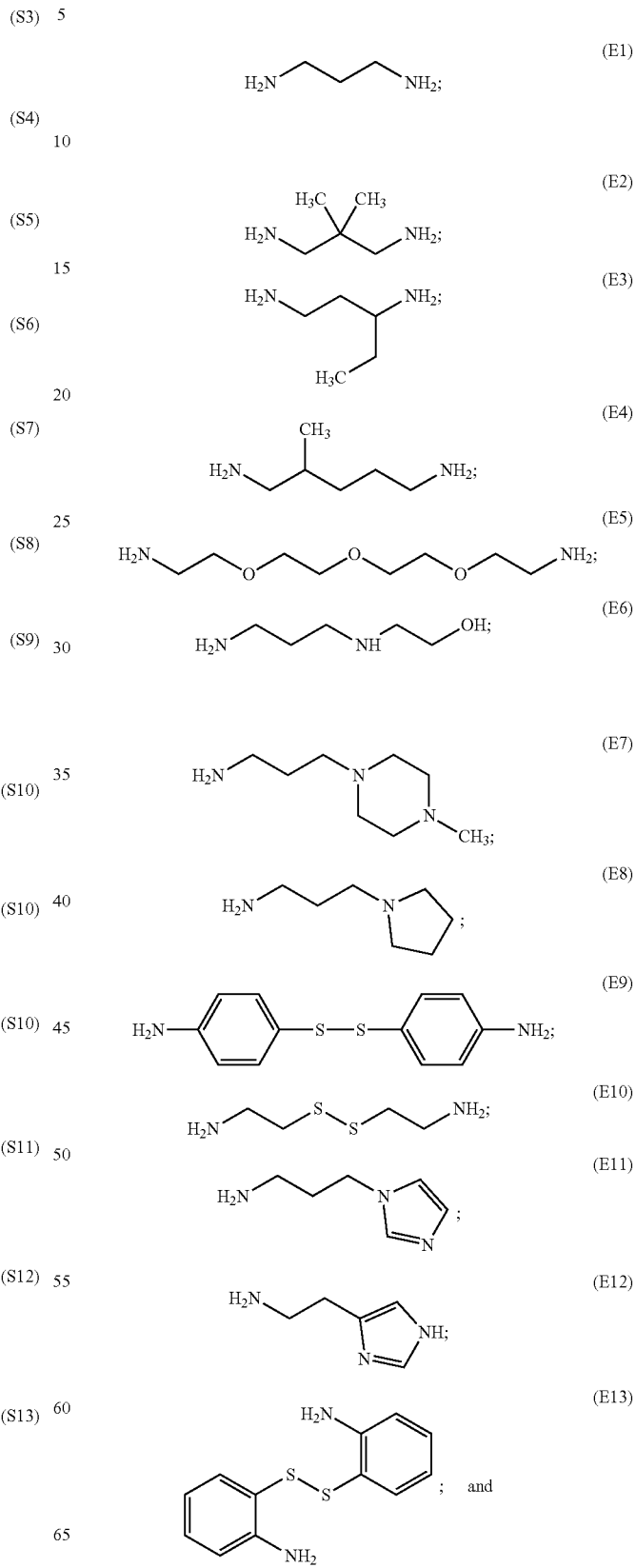

In yet other embodiments, R" is selected from the group consisting of:
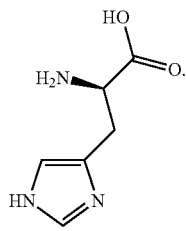
(E14)
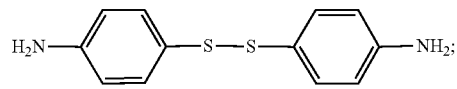
(E9)
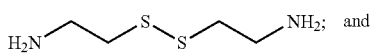
(E10)
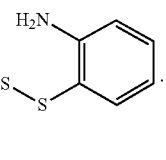
(E13)
In particular embodiments, the compound of formula (I) has a backbone comprising ester linkages and has the following structure:
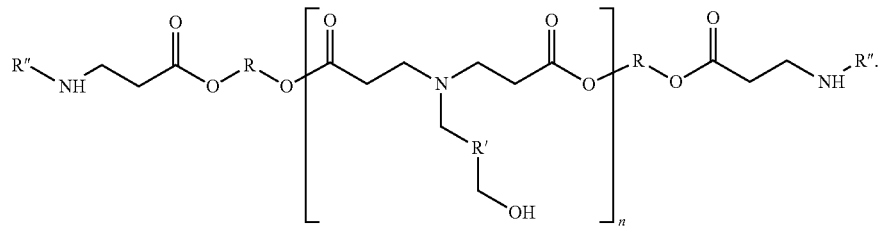
In other embodiments, the compound of formula (I) has a backbone comprising disulfide linkages and has the following structure:
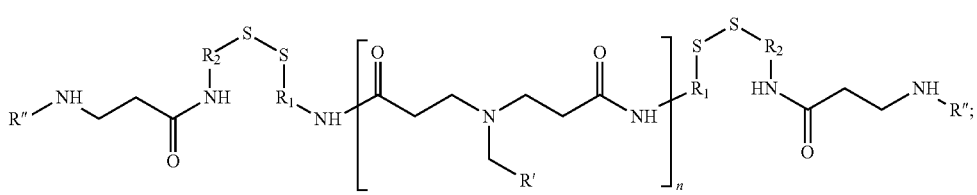

wherein $R_1$ and $R_2$ each independently are $C_1$-$C_{30}$ alkyl chains and R" comprises a non-reducible amino group independent from the structure of R' or —C—R'.
In certain embodiments, the non-reducible R" group is selected from the group consisting of:
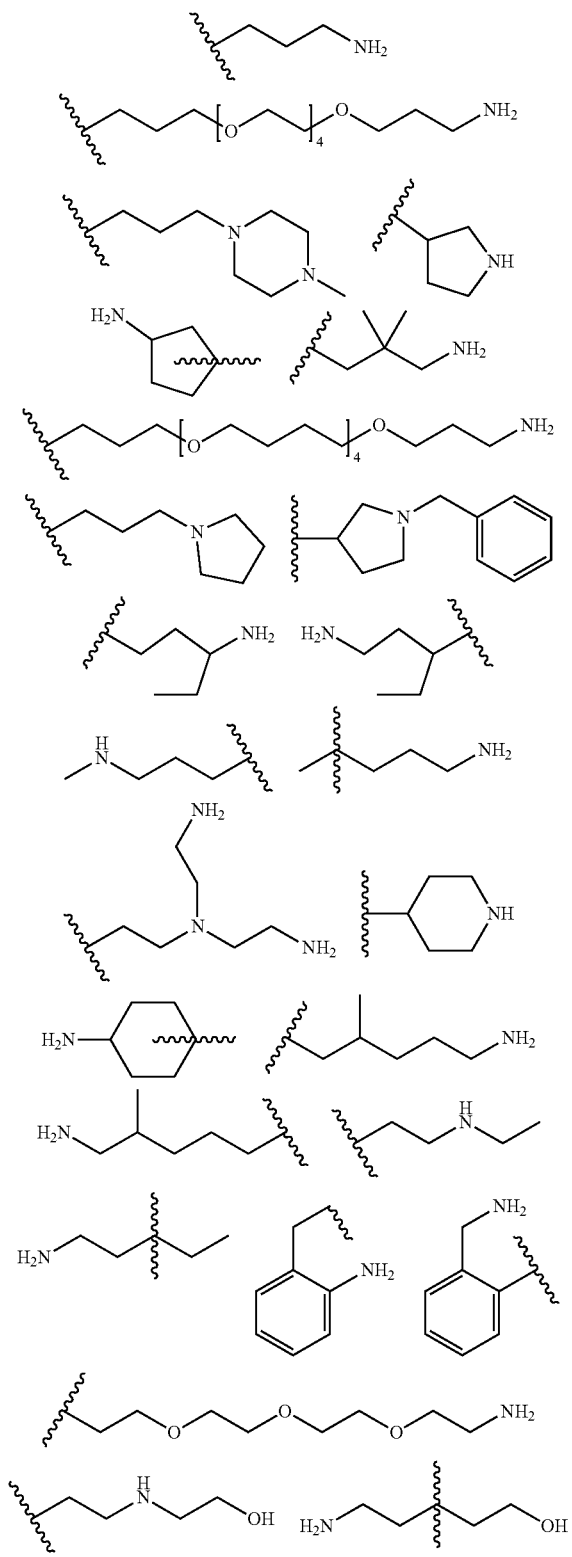
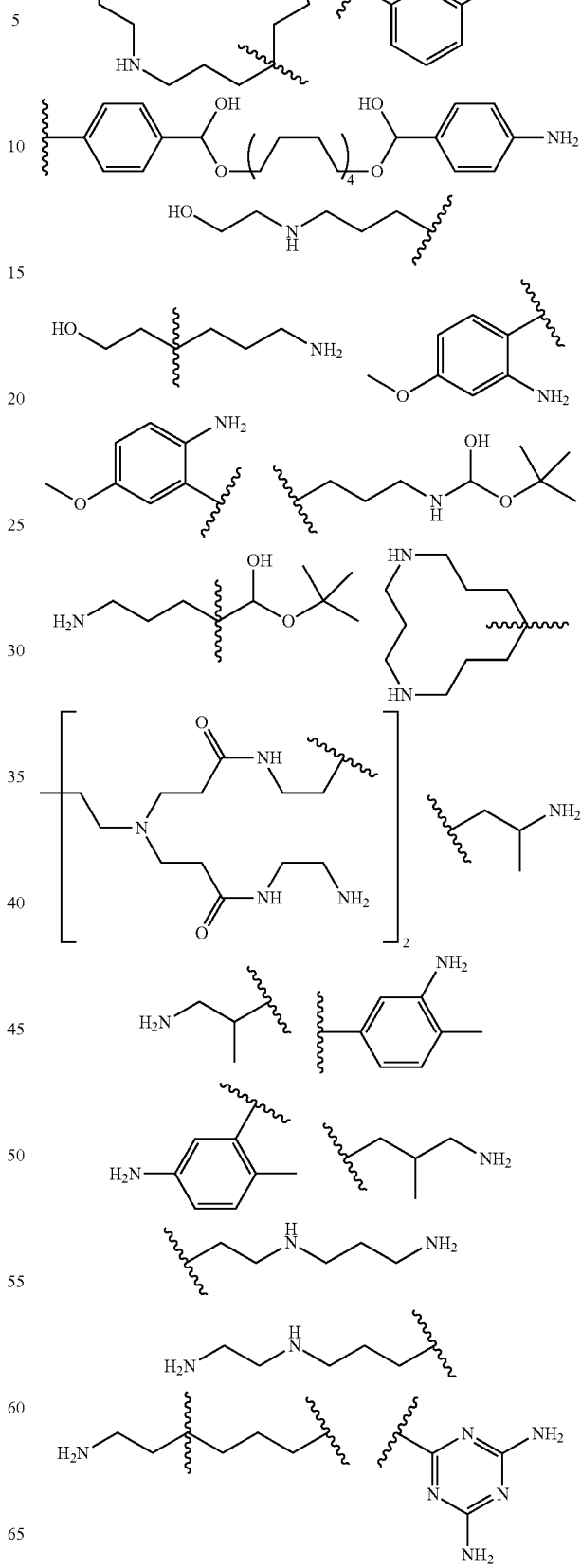

17
-continued
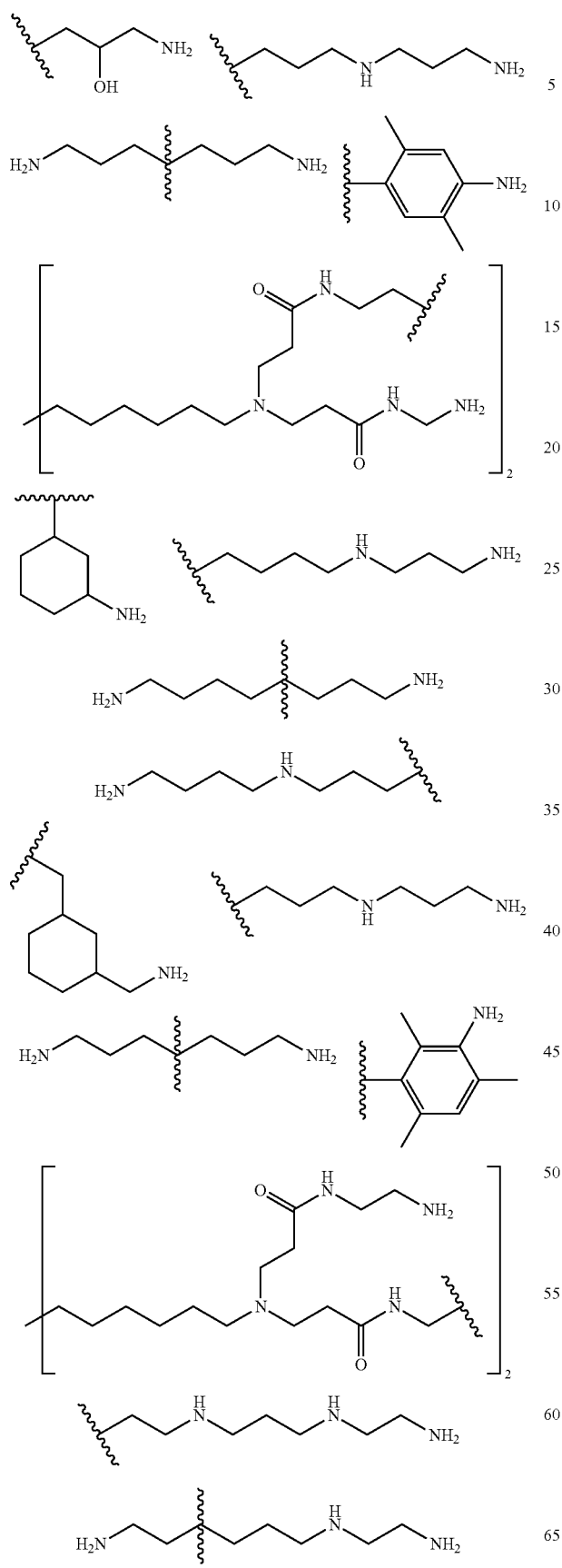
18
-continued
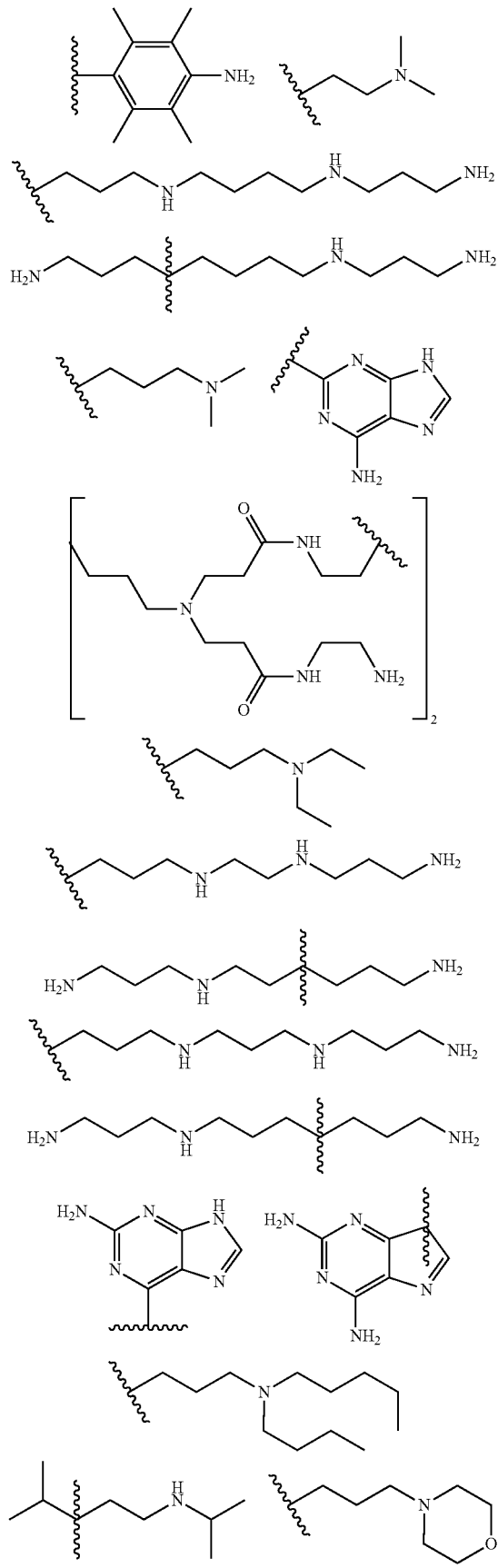

-continued
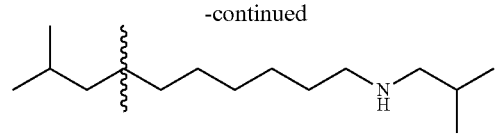
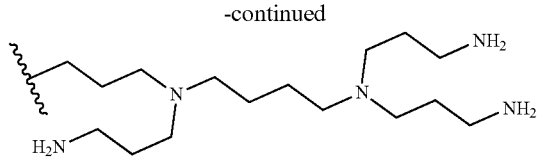
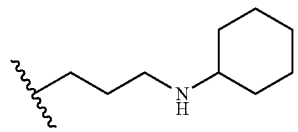
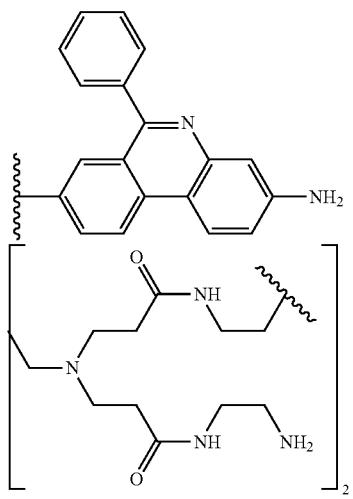
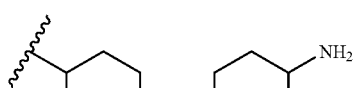
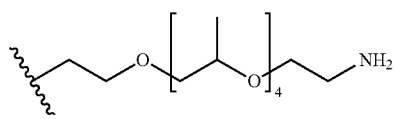
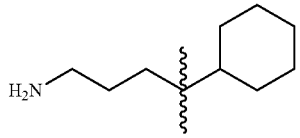
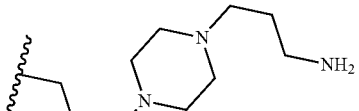
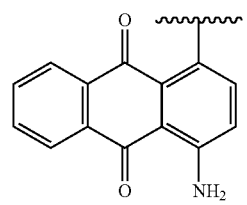
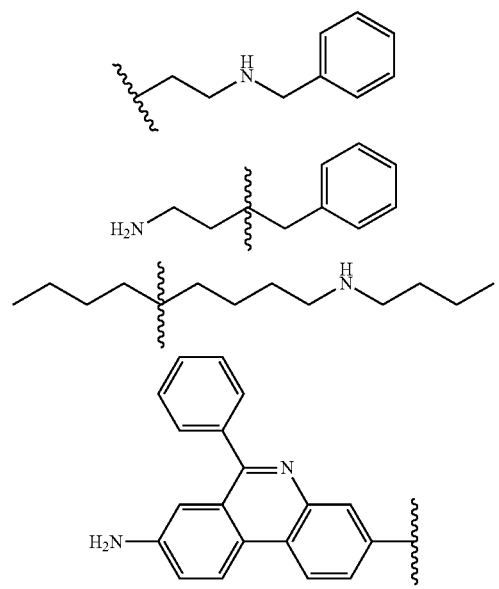
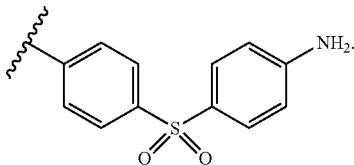
In yet other embodiments, the compound is a copolymer of a compound of formula (I), wherein the copolymer has the following structure:
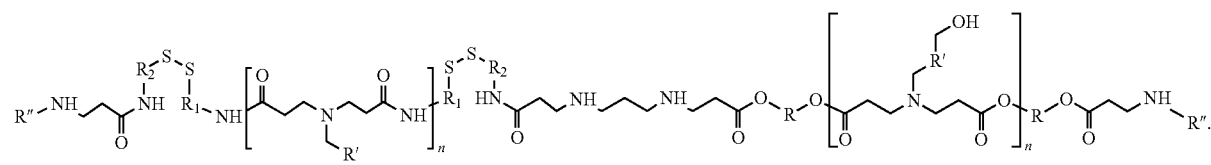

In certain embodiments, the copolymer comprises one or more monomers selected from the group consisting of:
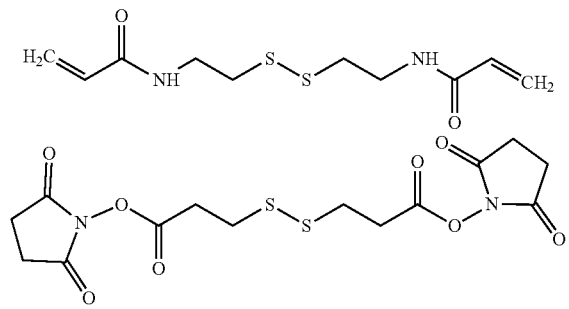
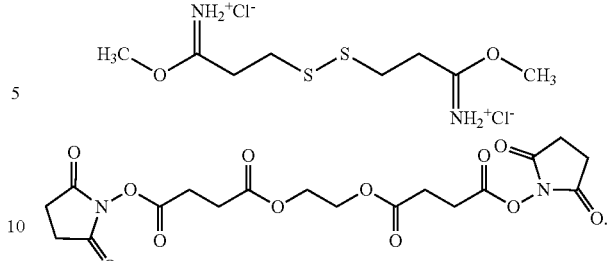
In yet more particular embodiments, the compound of formula (I) has a structure selected from the group consisting of:
B4-S5-E9
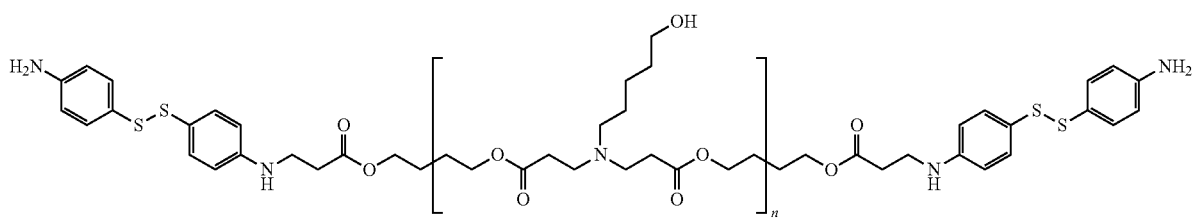
B3b-S4-E9
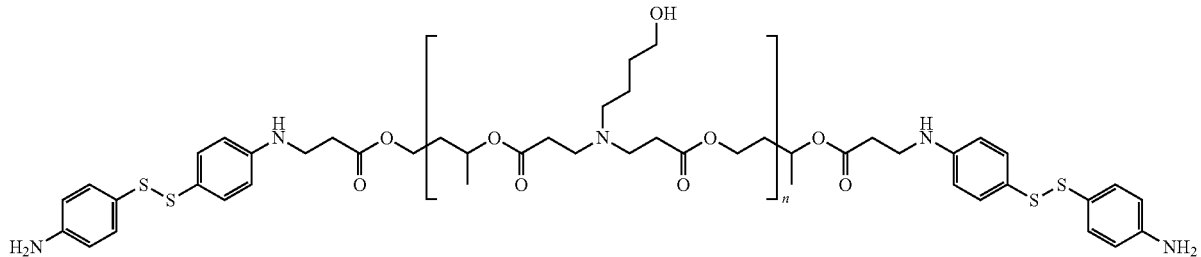
BL2-S5-E10
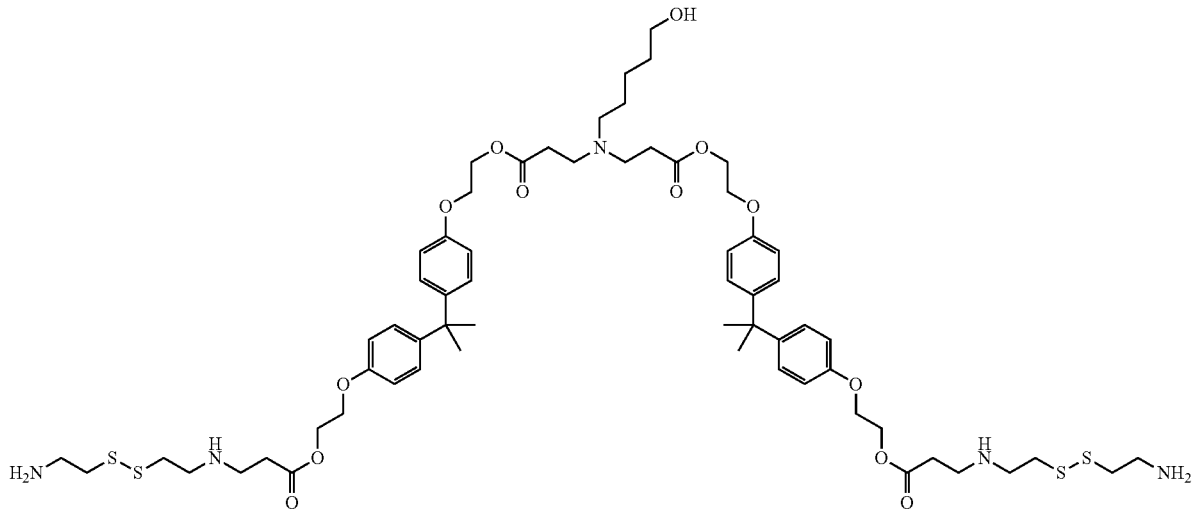

-continued
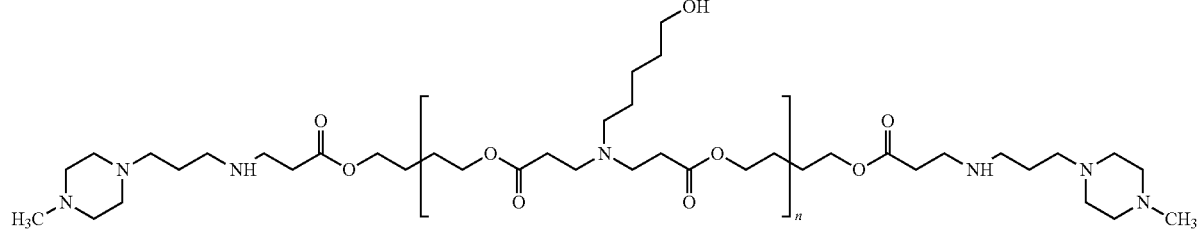
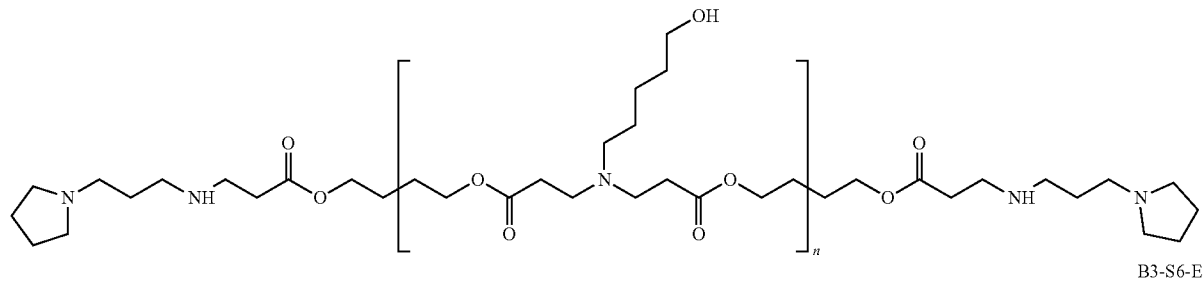
B3-S6-E7
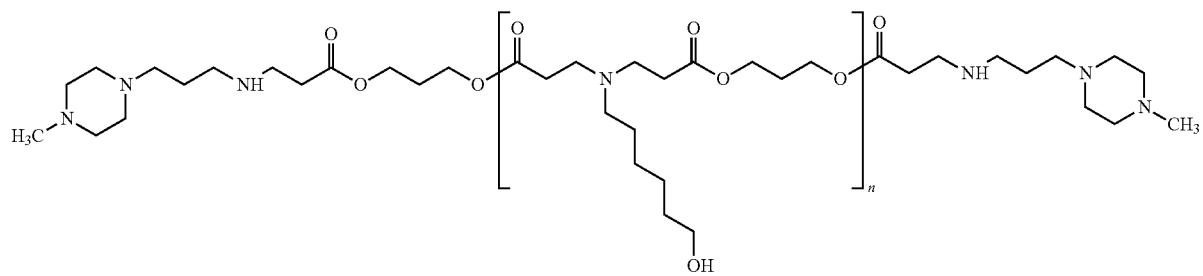
B5-S4-E10
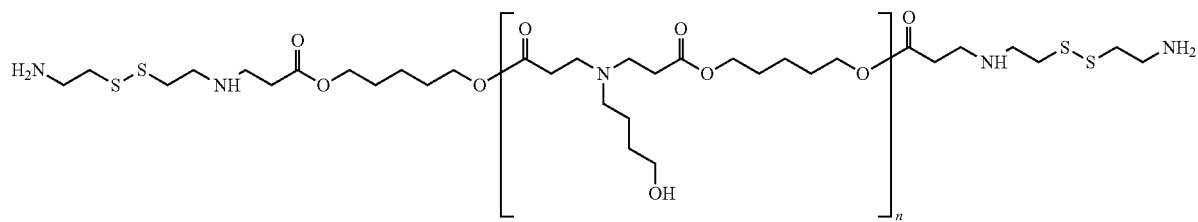
BSS-S3-E8
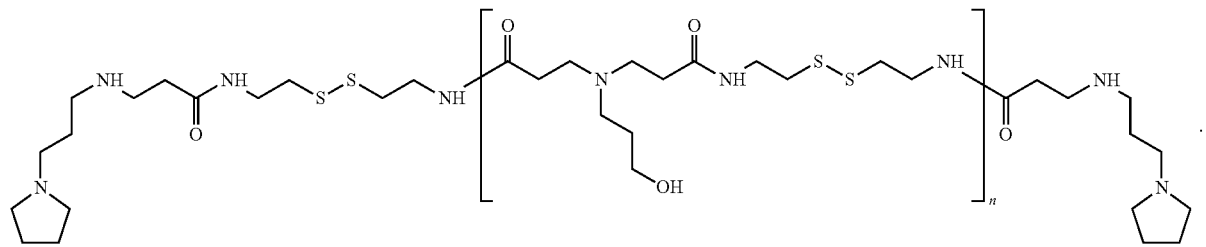
In some embodiments, the biodegradable nanoparticle or microparticle suitable for use with the presently disclosed methods comprises a PBAE of formula (I) as disclosed in U.S. Pat. No. 8,992,991:
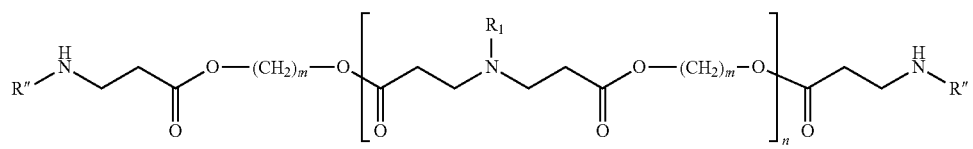

wherein:
  each m is independently an integer selected from the group consisting of 3, 4, 5, 6, and 8;
  n is an integer from 1 to 10,000;
  R' is a side chain comprising a functional group selected from the group consisting of —OH, —NH$_2$ and —SH; and
  R" is selected from the group consisting of:

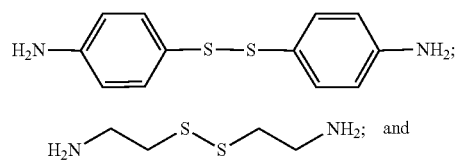
(E9)

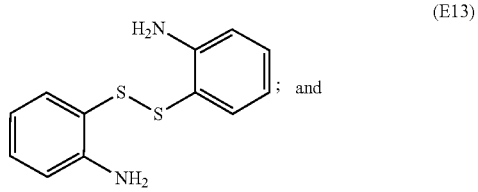
(E13)

; and pharmaceutically acceptable salts thereof.

In some embodiments, R' is selected from S3, S4, S5, S6, S7, S8, S9, S10, S11, S12, and S13 as provided hereinabove.

In particular embodiments, the compound of formula (I) has a structure selected from the group consisting of:

B3-S4-E9

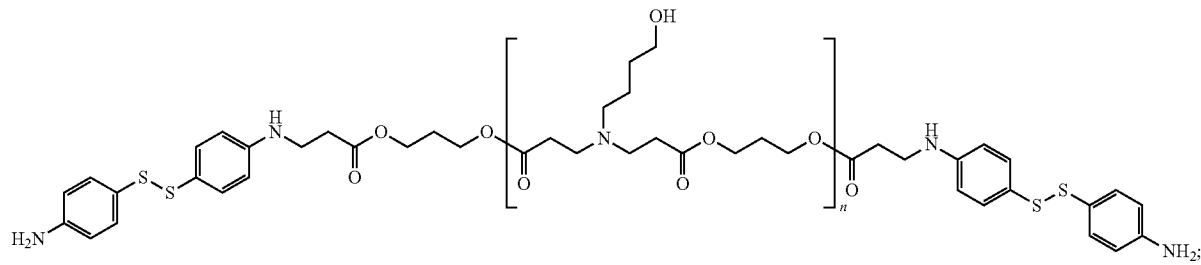

B4-S4-E9

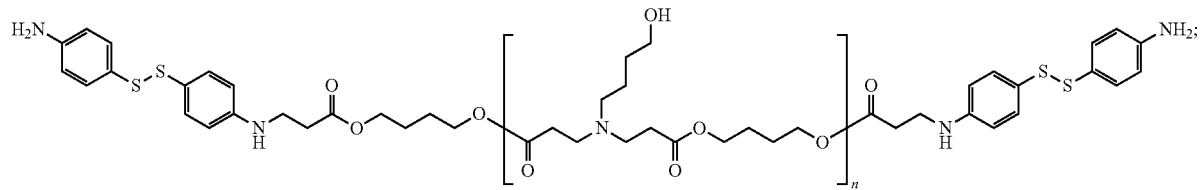

B4-S5-E9

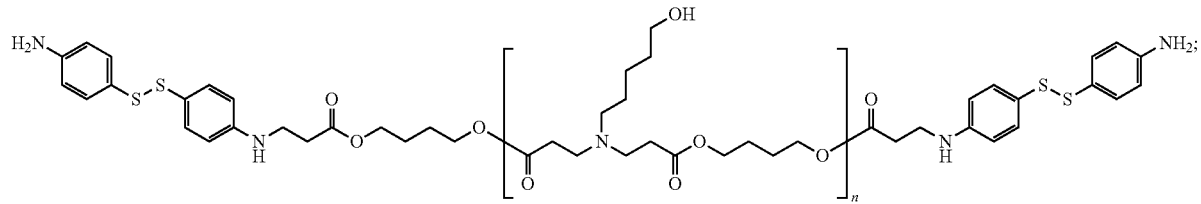

B5-S4-E9

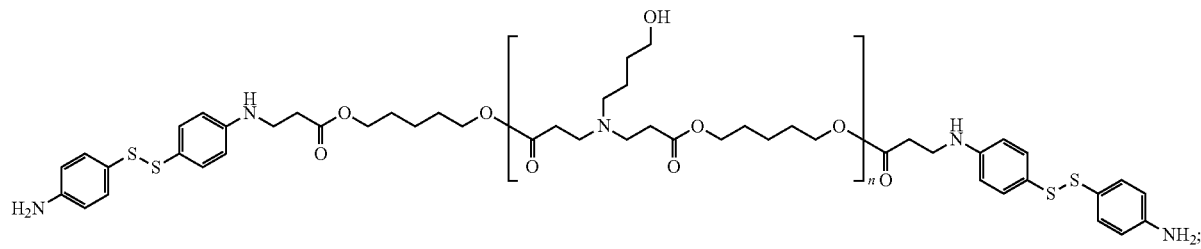

B3-S4-E10
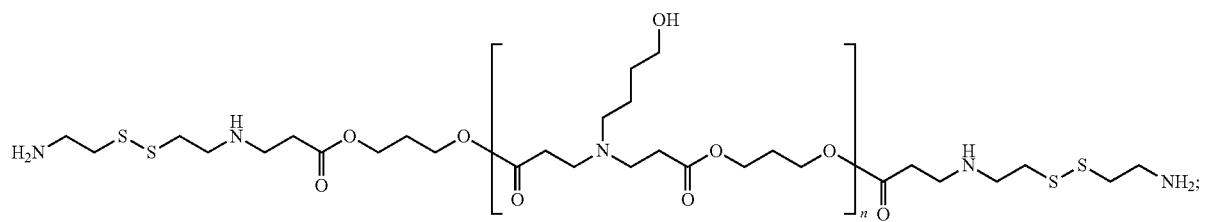
B4-S4-E10
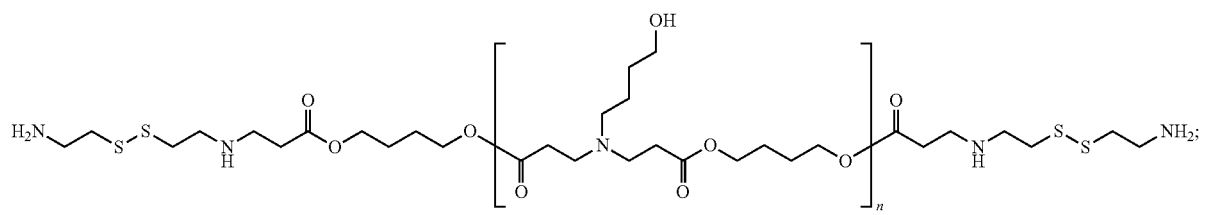
B4-S5-E10
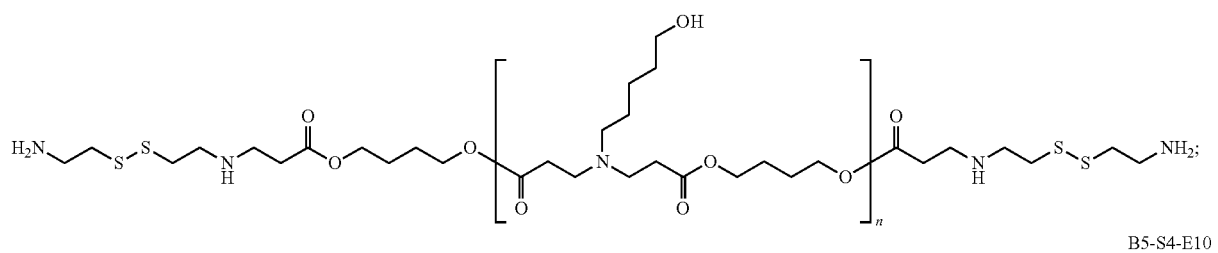
B5-S4-E10
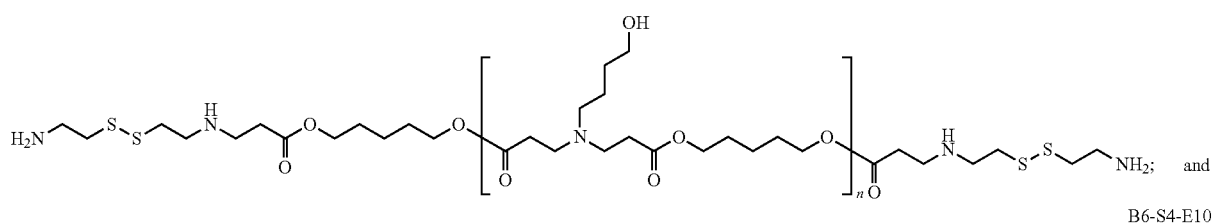
and
B6-S4-E10
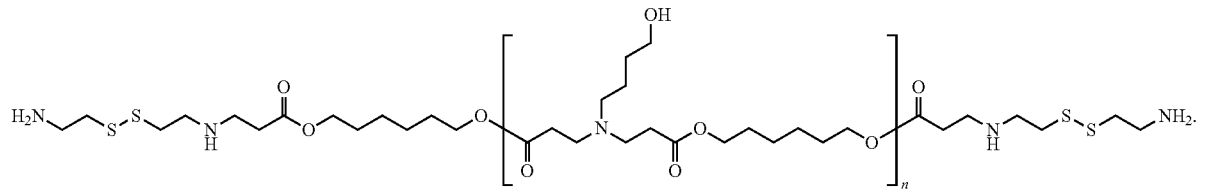
In some embodiments, the biodegradable nanoparticle or microparticle suitable for use with the presently disclosed methods comprises a PBAE of formula (I) as disclosed in U.S. patent application publication no. 20150250881:
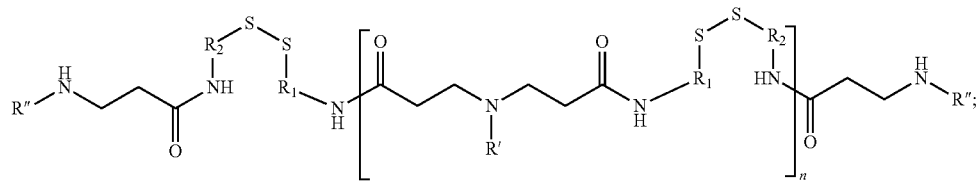

wherein: n is an integer from 1 to 10,000; each $R_1$ and $R_2$ are each independently $C_1$-$C_{30}$ alkylene chains; each R' independently comprises a functional group selected from the group consisting of —OH, —$NH_2$ and —SH; and each R" independently comprises a non-reducible amino group independent from R' or —C—R'.

In some embodiments, n is an integer selected from the group consisting of: an integer from 1 to 1,000; an integer from 1 to 100; an integer from 1 to 30; an integer from 5 to 20; an integer from 10 to 15; and an integer from 1 to 10.

In some embodiments, R' is selected from S3, S4, S5, S6, S7, S8, S9, S10, S11, S12, and S13 as provided hereinabove.

In some embodiments, the non-reducible R" group is selected from the non-reducible R" groups as provided hereinabove.

In some embodiments, the biodegradable nanoparticle or microparticle suitable for use with the presently disclosed methods comprises a PBAE of formula (I) or formula (II) as disclosed in U.S. patent application publication no. 20150273071:

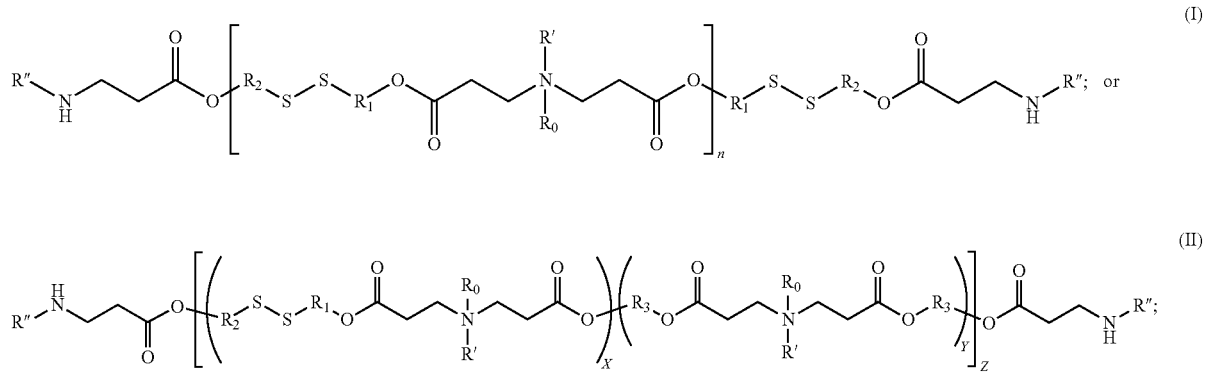

wherein:
n is an integer from 1 to 10,000;
X and Y are integers, which can be represented by a ratio X:Y;
Z is an integer from 1 to 10,000;
$R_0$ can be present or absent and when present the compound of formula (I) or formula (II) further comprises a counter ion selected from the group consisting of chloride, fluoride, bromide, iodide, sulfate, nitrate, fumarate, acetate, carbonate, stearate, laurate, and oleate;
$R_1$ and $R_2$ can be the same or different and are each independently a $C_1$-$C_{30}$ alkyl chain;
each $R_3$ is a $C_3$-$C_8$ linear or branched alkyl chain;
R' is a substituted side chain comprising a functional group that facilitates solubility in water and/or hydrogen bonding;
each R" can be the same or different and comprise a non-reducible end group or reducible end group; and pharmaceutically acceptable salts thereof.

In some embodiments, R' comprises a functional group selected from the group consisting of —OH, —$NH_2$ and —SH. In particular embodiments, R' is selected from S3, S4, S5, S6, S7, S8, S9, S10, S11, S12, and S13 as provided hereinabove.

In more particular embodiments, at least one R" comprises a $C_1$-$C_{30}$ alkyl chain. In yet more particular embodiments, the alkyl chain is terminated with a functional group selected from the group consisting of —OH and —$NH_2$.

In certain embodiments, R" comprises an end group selected from the group consisting of E1, E2, E3, E4, E5, E6, E7, E8, E9, E10, E11, E12, E13, and E14, as provided hereinabove.

In certain embodiments, R" comprises a non-reducible amino group independent from the structure of R' or —C—R'. In some embodiments, the non-reducible R" group is selected from the non-reducible R" groups as provided hereinabove.

In particular embodiments, the compound of formula (I) has the following structure:

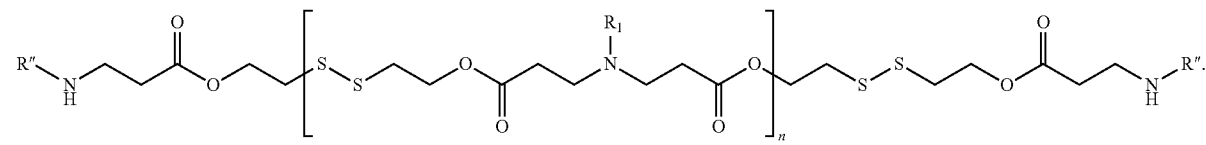

In yet more particular embodiments, the compound of formula (I) has the following structure:
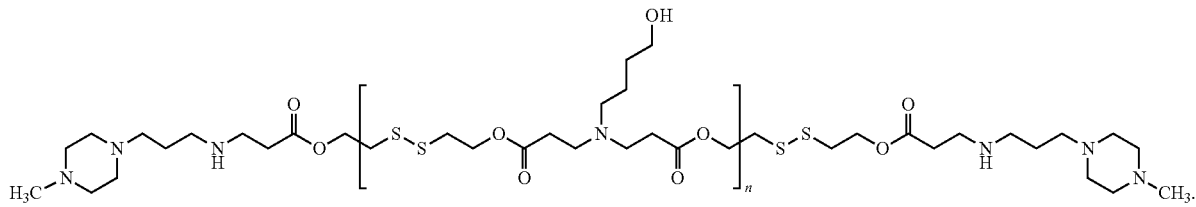
In certain embodiments, the compound of formula (II) is selected from the group consisting of:
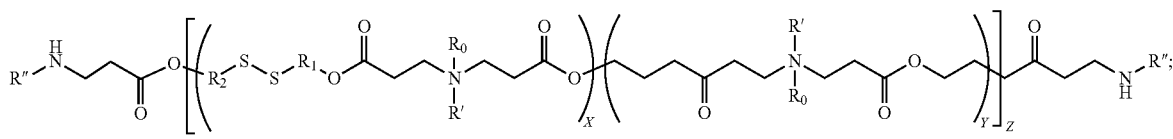
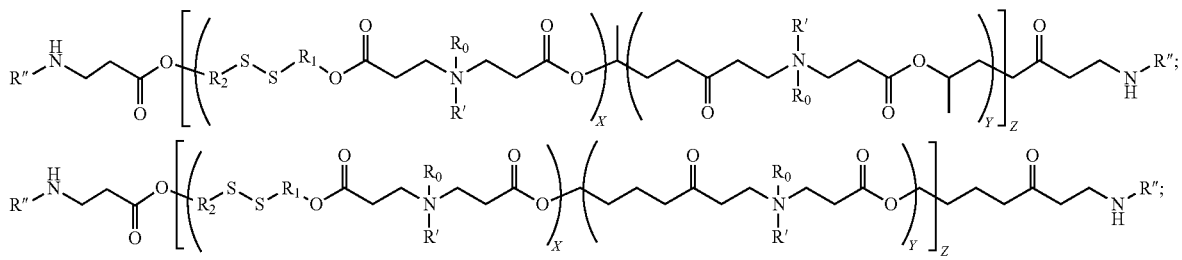
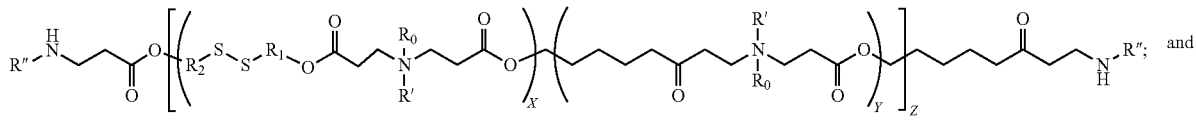
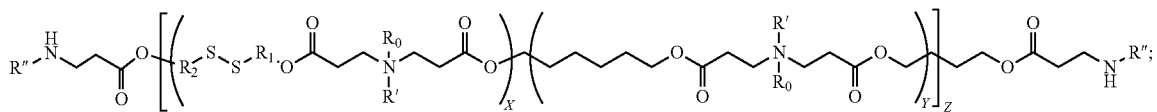
In yet more certain embodiments, the compound of formula (II) has the following formula:
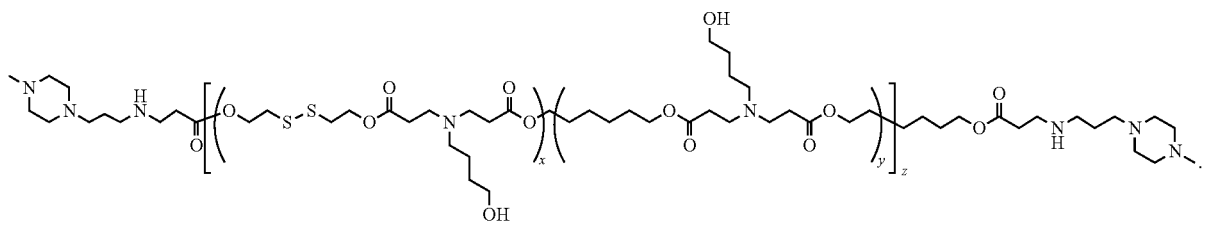

In some embodiments, the biodegradable nanoparticle or microparticle suitable for use with the presently disclosed methods comprises a PBAE of formula (I) as disclosed in U.S. patent application nos. 20120114759 and 20160374949.

In particular embodiments, the biodegradable nanoparticle or microparticle suitable for use with the presently disclosed methods comprises a PBAE of formula (I) as disclosed in U.S. Pat. No. 9,717,694:

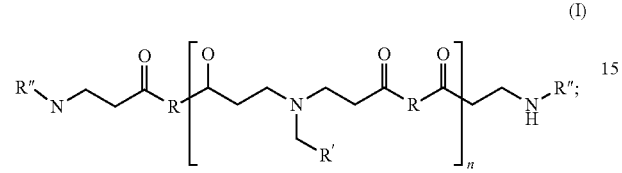
(I)

wherein: n is an integer from 1 to 10,000;
R is selected from the group consisting of:

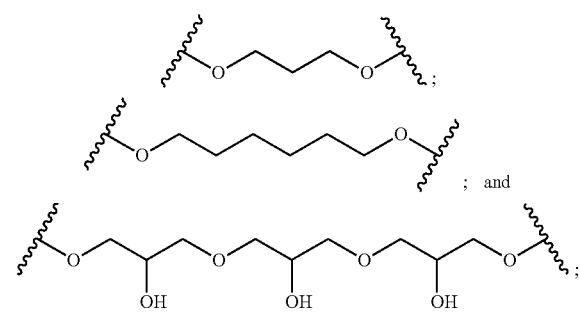
; and

R' is selected from the group consisting of:

; and

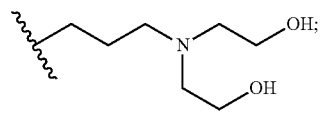

R" is selected from the group consisting of:

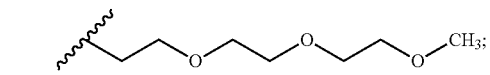

and poly(lactide-co-glycolide) (PLGA).

In particular embodiments, the PBAE has the following structure:

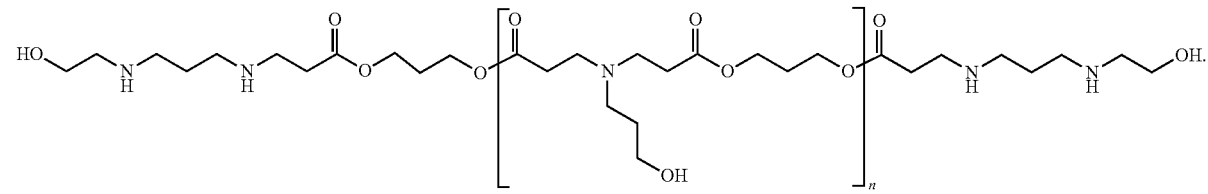

In some embodiments, the biodegradable nanoparticle or microparticle suitable for use with the presently disclosed methods comprises a polyethylene glycol (PEG)-b-poly(beta-amino ester) (PBAE) co-polymer (PEG-PBAE) of formula (I), as disclosed in WO2016/154622:

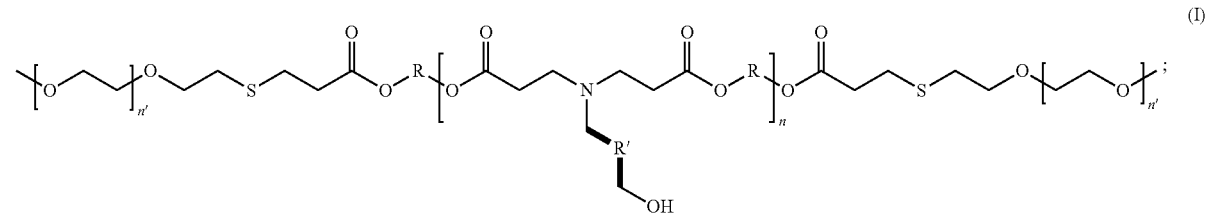
(I)

wherein: each n and n' is independently an integer from 1 to 10,000, 1 to 1,000, 1 to 100, 1 to 30, 5 to 20, 10 to 15, and 1 to 10; R is $C_2$ to $C_8$ substituted or unsubstituted linear or branched alkylene; and R' is $C_1$ to $C_5$ substituted or unsubstituted linear or branched alkylene, wherein each R and R' can independently be the same or different; and pharmaceutically acceptable salts thereof.

In particular embodiments of the presently disclosed PEG-PBAE co-polymer, the PEG subunit has a molecular weight selected from the group consisting of about 0.5 kDa to about 5 kDa, about 5 kDa to about 10 kDa, about 10 kDa to about 20 kDa, and about 20 kDa to about 30 kDa. Also in particular embodiments of the presently disclosed PEG-PBAE co-polymer, the PBAE subunit has a molecular weight ranging from about 1 kDa to about 5 kDa, 5 kDa to about 10 kDa, about 4 kDa to about 13 kDa, about 10 kDa to about 15 kDa, about 15 kDa to about 25 kDa, about 25 kDa to about 50 kDa, and about 50 kDa to about 100 kDa.

In certain embodiments of the PEG-PBAE co-polymer, the co-polymer is selected from the group consisting of: $PEG_{0.8k}\text{-}B4S4_{4k}\text{-}PEG_{0.8k}$, $PEG_{0.8k}\text{-}B4S4_{13k}\text{-}PEG_{0.8k}$, $PEG_{5k}\text{-}B4S4_{4k}\text{-}PEG_{5k}$, and $PEG_{5k}\text{-}B4S4_{13k}\text{-}PEG_{5k}$.

In other embodiments, the presently disclosed subject matter provides a particle comprising a blend of a polyethylene glycol (PEG)-b-poly(beta-amino ester) (PBAE) co-polymer of Formula (I) and a poly(beta-amino ester) (PBAE). In certain embodiments, the poly(beta-amino ester) (PBAE) comprises an unmodified poly(beta-amino ester) (PBAE).

B. Nonviral Gene Transfer to the Suprachoroidal Space i. Nonviral Suprachoroidal Gene Transfer for Delivery of Therapeutic Genes, Including Anti-VEGF Agents, for Treating Retinal and Choroidal Vascular Diseases In some embodiments, the presently disclosed subject matter demonstrates that it is possible to transduce cells of the retina, such as photoreceptors (e.g., cone cells and rod cells), retinal ganglion cells, amacrine cells, Müller cells, astrocytes, bipolar cells, horizontal cells, retinal pigment epithelium cells (RPE), and cells of the sclera, and the choroid, by suprachoroidal injection of PBAE nanoparticles containing an expression construct. In some embodiments, the presently disclosed methods may be used for gene delivery of therapeutic transgenes to the retina. A representative example is a protein that neutralizes vascular endothelial growth factor (VEGF). Intraocular injection of VEGF-neutralizing proteins is standard care for neovascular age-related macular degeneration (NVAMD), diabetic macular edema (DME), and macular edema occurring after retinal vein occlusion (RVO) (Campochiaro, et al., Ophthalmology, 2016). Suprachoroidal injection of an expression construct for a VEGF-neutralizing protein may provide sustained expression in the retina and choroid where it is needed.

One advantage of nonviral gene transfer over gene transfer with viral vectors is that the former does not induce an immune response and therefore repeated injections are possible. Suprachoroidal injections are relatively noninvasive and can be done in an outpatient clinic as opposed to subretinal injection of viral vectors, which requires an operative procedure, and which carries a 1% risk of retinal detachment, a vision threatening complication. Further, the longer the duration of expression the more useful this invention will be for gene replacement and for gene delivery.

Other therapeutic transgenes that could be delivered by the presently disclosed methods include, but are not limited to, neutralizing proteins for vascular endothelial-protein tyrosine phosphatase (VE-PTP). Blocking VE-PTP activates Tie2 (Shen, et al., 2014) and when combined with VEGF suppression in patients with diabetic macular edema, the effect is greater than with VEGF suppression alone (Campochiaro, et al., Ophthalmology, 123(8), 2016).

Another advantage of the presently disclosed approach is a large capacity, which allows simultaneous delivery of multiple transgenes. Further, since photoreceptors are transduced, another potential application of the presently disclosed methods is gene replacement of mutated genes in photoreceptors causing retinal degenerations.

In other embodiments, the presently disclosed methods may also be used with CRISPR/Cas9 technology. In such embodiments, transient expression may be more useful so that once the target site is edited, there is less chance for off target effects. PBAE formulations, such as those incorporated by reference hereinabove, that efficiently compact RNA into nanoparticles have been identified and are well-suited to deliver mRNA for the guide strand and nuclease to provide transient targeted gene editing with minimal chance of off-target effects.

Accordingly, the presently disclosed subject matter has the potential to provide a noninvasive sustained delivery of therapeutic proteins to the retina and choroid, or replacement of mutated genes in retinal cells, such as photoreceptors. It also provides a means for transient targeted gene editing by transient nuclease expression in photoreceptors.

ii. Gene Replacement for Inherited Retinal Degenerations

The current approach for gene replacement of inherited retinal degenerations is subretinal injection of viral vectors. Suprachoroidal injection of nonviral vectors, however, has the following advantages.

Subretinal injection of viral vectors results in detachment of the photoreceptors from the RPE, while suprachoroidal injection of nonviral vectors does not result in such detachment. This characteristic is a major advantage of suprachoroidal injection over subretinal injection because detaching the photoreceptors from the RPE is damaging to photoreceptors, particularly in eyes with retinal degeneration in which the photoreceptors are already compromised. Also, eyes with retinal degeneration have subretinal fibrosis and the photoreceptors are more adherent to the RPE, so it can be difficult to inject into the subretinal space and when it is done, it can be complicated by macular holes.

Further, unlike subretinal injection, which must be done in the operating room as part of an operation called vitrectomy, suprachoroidal nonviral gene transfer can be done in an outpatient clinic. Vitrectomy causes cataract in a high percentage of patients and there is a 1-2% risk of retinal detachment. As a result, suprachoroidal injections are safer, less expensive, and more convenient than subretinal injections.

Also, spread of vector in the suprachoroidal space is greater than spread in the subretinal space, thereby allowing treatment of a larger portion of the retina with a single injection. This characteristic means more photoreceptors can have the defective gene replaced and salvaged, which should translate into better visual outcomes.

Unlike injection viral vectors, which cause an immune response and can only be done once, nonviral gene transfer does not cause an immune response and can be repeated. Thus, if the initial response is insufficient, it can be boosted by repeated injection.

Finally, the nanoparticles used for nonviral gene transfer have much greater capacity than AAV vectors and therefore can be used to replace larger genes or can be used to incorporate multiple genes. This characteristic is particularly useful for replacement of the Stargardt Disease gene, which is very large.

Accordingly, in some embodiments, the presently disclosed subject matter provides a method for gene replacement of inherited retinal degenerations, the method comprising administering to the suprachoroidal space a composition comprising a presently disclosed nanoparticle or microparticle and a gene associated with inherited retinal degenerations. In some embodiments, the nanoparticles encapsulate plasmids that encode genes that replace defective genes due to inherited retinal diseases, including, but not limited to, RPE65, BEST1, NR2E3, NRL, RHO, RP1, and/or other autosomal dominant or autosomal recessive genes. In other embodiments the nanoparticles encapsulate X-linked genes, including, but not limited to, RPGR, RP2, or OFD1.

The presently disclosed method can be used, for example, to treat one or more diseases selected from the group consisting of Stargardt Disease, Choroideremia, Achromatopsia, and X-linked retinitis pigmentosa.

iii. Delivery of Therapeutic Proteins to Prevent Cone Cell Death in Patients with Retinitis Pigmentosa (RP)

Retinitis pigmentosa (RP) is a particular type of inherited retinal degeneration in which one of many different mutations causes rod photoreceptors to die. After rods die, the level of oxygen in the outer retina becomes markedly elevated because rods normally constitute 95% of cells in the outer retina and consume most of the oxygen. The high level of oxygen causes progressive oxidative damage to cones causing gradual cone cell death.

Cone cell death can be slowed or prevented by antioxidants and/or neuroprotective agents. Nrf2 is a transcription factor that upregulates several components of the antioxidant defense system and subretinal injection of a viral vector that expresses Nrf2 has been shown to reduce cone cell death in a model of RP. Glial cell line-derived neurotrophic factor (GDNF) is a survival factor for photoreceptors and other neurons and subretinal injection of a viral vector that expresses GDNF has been shown to reduce cone cell death in a model of RP.

Suprachoroidal injection of nanoparticles containing expression plasmids for Nrf2 and GDNF should promote cone survival and function better than subretinal injection of viral vectors that express Nrf2 or GDNF and, as provided hereinabove, can be given multiple times to boost expression and further improve outcomes.

Accordingly, in some embodiments, the presently disclosed subject matter provides a method for delivering therapeutic proteins to prevent cone cell death in patients with retinitis pigmentosa (RP), the method comprising administering to the suprachoroidal space a composition comprising a presently disclosed nanoparticle or microparticle and a therapeutic protein associated with cone cell death in patients with retinitis pigmentosa (RP). In such embodiments, the presently disclosed nanoparticles encapsulate plasmids that encode NRF2, GDNF, or other genes known to one skilled in the art that are neuroprotective to the retina. The presently disclosed method can be used for all patients with RP regardless of the causative mutation.

II. Compositions

Disclosed herein are compositions that may include a therapeutic agent and a nanoparticle and/or a microparticle. The composition may be a pharmaceutical composition when the composition includes a pharmaceutically acceptable carrier. The therapeutic agent may comprise, for example, a drug, small molecule, nucleic acid sequence, amino acid sequence, gene, transgene, peptide, protein, an expression vector, a small molecule, carbohydrate, lipid, sugar, antibody or antibody fragment thereof, hormone, hormone receptor, receptor ligand, and/or cancer cell specific ligands. In preferred embodiments, the therapeutic agent may be a gene, nucleic acid, expression vector, DNA, RNA, siRNA, microRNA, mRNA, or cyclic dinucleotides. The pharmaceutical compositions of the present disclosure can be formulated according to known methods for preparing pharmaceutically useful compositions.

As used herein, the terms "nucleic acid" and "nucleic acid sequence" refer to at least two nucleotides covalently linked together. The depiction of a single strand also defines the sequence of the complementary strand. Thus, an oligonucleotide also encompasses the complementary strand of a depicted single strand. An oligonucleotide also encompasses substantially identical nucleic acids and complements thereof. Oligonucleotides can be single-stranded or double-stranded, or can contain portions of both double-stranded and single-stranded sequences. The nucleic acid can be DNA, both genomic and complimentary DNA (cDNA), RNA, or a hybrid, where the nucleic acid can contain combinations of deoxyribo- and ribonucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods. A particular nucleic acid sequence can encompass conservatively modified variants thereof (e.g., codon substitutions), alleles, orthologs, single nucleotide polymorphisms (SNPs), and complementary sequences as well as the sequence explicitly indicated.

Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes. The composition may comprise a pharmaceutically acceptable carrier to formulate the compounds herein disclosed for the practice of the disclosure into dosages suitable for administration within the scope of the disclosure. The compounds can be formulated readily using pharmaceutically acceptable carriers well known in the art. Such carriers enable the compounds of the disclosure to be formulated as tablets, pills, and capsules, which may be dissolved in a liquid, or formulated as liquids, gels, syrups, slurries, suspensions and the like, for administration to a subject to be treated.

As discussed above, the compositions and/or pharmaceutical compositions may comprise a nanoparticle, a microparticle, or a combination thereof, in the delivery of the therapeutic agent. The term "particle" as used herein is meant to include nanoparticles and microparticles. As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). The term "microparticle" includes particles having at least one dimension in the range of about one micrometer (μm), i.e., $1\times10^{-6}$ meters, to about 1000 μm. In certain embodiments, the composition and/or pharmaceutical composition may comprise one or more nanoparticles, one or more microparticles, or a combination thereof. The nanoparticles and/or microparticles may comprise one or more poly (beta-amino ester)s (PBAEs), one or more polyethylene glycol-b-poly (beta-amino ester)s (PEG-PBAEs), or a combination thereof, as disclosed herein.

In some embodiments, the therapeutic agent is packaged in one or more nanoparticles, one or more microparticles, or combinations thereof. In some embodiments, one or more therapeutic agents are packaged in one or more nanoparticles, one or more microparticles, or combinations thereof. For example, a composition may comprise a first therapeutic agent packaged in a first particle, and a second therapeutic agent packaged in a second particle. In another example, a composition may comprise a first and a second therapeutic agent packaged into one particle. A particle may comprise 1, 2, 3, 4, 5, 6, 7, 8, 9, 10, or more different therapeutic agents. In preferred embodiments, the therapeutic agents may be one or more genes, nucleic acids, expression plasmids, DNA, RNA, siRNA, microRNA, mRNA, cyclic dinucleotides or combinations thereof.

In some embodiments, the microparticle or nanoparticle has an aspect ratio ranging from about 1 to about 5. In some embodiments, the aspect ratio has a range from about 5 to about 10. In some embodiments, the aspect ratio has a range from about 10 to about 100.

The suprachoroidal injection may be used to deliver a therapeutic agent to one or more cell types in the retina, for example, the therapeutic agent may be targeted to 1, 2, 3, 4, 5, 6, 7, 8, or more cell types in the eye. For example, the therapeutic agent may be targeted to one or more of photoreceptor cells (e.g., cone cells and rod cells), retinal ganglion cells, amacrine cells, Müller cells, astrocytes, bipolar cells, horizontal cells, retinal pigment epithelium cells (RPE), cells in the sclera, and/or cells in the choroid. In one aspect of the invention, the photoreceptors may be targeted for delivery of a therapeutic agent. In another aspect of the invention, the photoreceptors and retinal pigment epithelial cells may be targeted for delivery of a therapeutic agent. In another aspect of the invention, photoreceptors and retinal pigment epithelial cells may be targeted for delivery of one or more therapeutic agents.

In embodiments, the nanoparticles or microparticles will localize to one or more cell types. For example, the particle may localize to photoreceptor cells, delivering the therapeutic agent to the photoreceptor cells. In other embodiments, the particle may localize to photoreceptor cells and Muller cells, delivering the therapeutic agent to the photoreceptor cells and the Muller cells.

In an embodiment, the therapeutic agent may be a drug, small molecule, nucleic acid sequence, amino acid sequence, gene, transgene, peptide, protein, expression vector, carbohydrate, lipid, sugar, antibody or antibody fragment thereof, hormone, hormone receptor, receptor ligand, and/or a cancer cell specific ligand. An "expression construct" or an "expression vector" is a plasmid derived from a bacterial or viral genome designed for the expression of one or more genes in a cell.

III. Methods of Treatment

Provided herein are methods of treating a subject with a disease or condition of the eye, comprising administering to the suprachoroidal space a composition comprising a nanoparticle or microparticle and a therapeutic agent. In another embodiment, the method may comprise preparing a composition comprising a pharmaceutically acceptable carrier and a nanoparticle or a microparticle, wherein the nanoparticle or microparticle comprises a therapeutic agent, and administering the composition to the suprachoroidal space of the eye.

In certain embodiments, the therapeutic agent may be administered to treat a subject with an injury, disease, or condition of the eye. The terms "subject" and "patient" are used interchangeably herein. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease.

The therapeutic agent may be used to treat a subject with a disease, such as, for example, macular degeneration (AMD), retinitis pigmentosa, optic neuritis, an infection, uveitis, sarcoid, sickle cell disease, retinal detachment, temporal arteritis, retinal ischemia, choroidal ischemia, choroidal ischemia, ischemic optic neuropathy, arteriosclerotic retinopathy, hypertensive retinopathy, retinal artery blockage, retinal vein blockage, glaucoma, hypotension, diabetic retinopathy, macular edema, retinal vein occlusion, or choroidal neovascularization.

The term "administration" or "administering" is used throughout the specification to describe the process by which the disclosed compositions may be delivered to a subject. Administration will often depend upon the amount of composition administered, the number of doses, and duration of treatment. Multiple doses of the composition may be administered. The frequency of administration of the composition can vary depending on any of a variety of factors, such as the level of the therapeutic agent in the ocular tissues, and the like. The duration of administration of the composition, e.g., the period of time over which the composition is administered, can vary, depending on any of a variety of factors, including patient response, etc.

The therapeutic agent may be delivered in a therapeutically effective amount. A "therapeutically effective amount," or "effective dosage" or "effective amount" as used interchangeably herein unless otherwise defined, means a dosage of a drug effective for periods of time necessary, to achieve the desired therapeutic result. An effective dosage may be determined by a person skilled in the art and may vary according to factors such as the disease state, age, sex, and weight of the individual, and the ability of the drug to elicit a desired response in the individual. This term as used herein may also refer to an amount effective at bringing about a desired in vivo effect in an animal, vertebrate, mammal, or human, such as increasing the time until anesthetic induction.

The therapeutic agent may be administered at varying dosages depending on the subject, disease, etc. The composition may be administered at a dosage of from about 0.00001 mg/kg to about 10 mg/kg, such as from about 0.0001 mg/kg to about 9 mg/kg, from about 0.001 mg/kg to about 8 mg/kg, from about 0.01 mg/kg to about 7 mg/kg, from about 0.1 mg/kg to about 6 mg/kg, from about 1 mg/kg to about 5 mg/kg, or from about 2 mg/kg to about 4 mg/kg. In certain embodiments, the composition is administered at a dosage of less than or equal to about 10 mg/kg, less than or equal to about 8 mg/kg, less than or equal to about 6 mg/kg, less than or equal to about 4 mg/kg, less than or equal to about 2 mg/kg, less than or equal to about 1 mg/kg, less than or equal to about 0.1 mg/kg, less than or equal to about 0.001 mg/kg, or less than or equal to about 0.0001 mg/kg. In certain embodiments, the composition may be administered at a dosage of greater than or equal to about 0.0001 mg/kg, greater than or equal to about 0.01 mg/kg, greater than or equal to about 3 mg/kg, greater than or equal to about 5 mg/kg, greater than or equal to about 7 mg/kg, or greater than or equal to about 9 mg/kg.

The composition may be administered a varying amount of times depending on the subject, disease, etc. For example, the composition may be administered 1 to 4 times daily for a period of, for example 1 to 10 years, at any suitable interval. The composition may also be administered over a period of 1 day, 10 days, 1 month, 6 months, 12 months, 5 years, or 10 years, at any suitable interval that can allow for an accurate analysis of the subject. For example the composition may be administering 1, 2, 3, 4, 5, 6, 7, 8, 9, 10, or more times over 1 day, 1 week, 4 weeks, 2 months, 3 months, 4 months, 5 months, 6 months, 7 months, 8 months 9 months, 10 months, 11 months, 12 months, 2 years, 3 years, 4 years, 5 years, 6 years, 7 years, 8 years, 9 years, or 10 years. During the time frame that the method is being performed, the step of observing and/or quantifying the delivery of the therapeutic agent in the subject's eye can be performed any suitable number of times. For example, in embodiments the method is performed for at least 6 months, the step of observing and/or quantifying the therapeutic agent can be performed once daily, twice daily, once every 2 days, once every 3 days, etc.

The dosage and time for administering the composition can vary according to factors such as the degree of susceptibility of the individual, the age, sex, and weight of the individual, idiosyncratic responses of the individual, the dosimetry, and the like. Detectably effective amounts of the composition of the present disclosure can also vary according to instrument and film-related factors. Optimization of such factors is well within the level of one of skill in the art.

In certain embodiments, the therapeutic agent may neutralize the activity of a protein, stimulate the activity of a protein, or a combination thereof. For example, the therapeutic agent may neutralize the activity of one or more proteins, and stimulate the activity of one or more proteins. In another example, the therapeutic agent may neutralize the activity of two or more proteins. In another embodiment, the therapeutic agent may stimulate the activity of two or more proteins. The therapeutic agent may neutralize or stimulate one or more growth factors. Such growth factors may be, for example, angiopoietin 2 (Angpt2), fibroblast growth factor (FGF), insulin and insulin-like growth factor (IGF), transforming growth factor-beta (TGFB), platelet-derived growth factor (PDGF), nerve growth factor (NGF), epidermal growth factor (EGF), colony-stimulating factor (CSF), vascular endothelial growth factor (VEGF), or a combination thereof.

IV. Kits

In certain embodiments, the disclosed kits comprise one or more containers, including, but not limited to a vial, tube, ampule, bottle and the like, for containing the pharmaceutical composition including a reagent containing the nanoparticles, macroparticles, and/or the therapeutic agents. The reagent may be present solvated, in suspension, or powder form, and may then be reconstituted in the pharmaceutically acceptable carrier to provide the pharmaceutical composition. The one or more containers also can be carried within a suitable carrier, such as a box, carton, tube or the like. Such containers can be made of plastic, glass, laminated paper, metal foil, or other materials suitable for holding medicaments.

In certain embodiments, the container can hold a pharmaceutical composition and may have a sterile access port (for example the container may be an intravenous solution bag or a vial having a stopper pierceable by a hypodermic injection needle). Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The disclosed kits also can include associated instructions for using the reagent.

V. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Suprachoroidal Nonviral Gene Transfer

The presently disclosed subject matter demonstrates that it is possible to achieve good expression of a reporter gene by suprachoroidal injection of an expression plasmid packaged in biodegradable polymeric nanoparticles.

For example, FIG. 1 shows strong expression of green fluorescent protein (GFP) in the retina of a rat 2 weeks after suprachoroidal injection of a GFP expression construct packaged in nanoparticles. Comparison with sections stained with hematoxylin and eosin (FIG. 2) suggest that GFP is located in the photoreceptor inner and outer segments, and Muller cells.

More particularly, in some embodiments, the presently disclosed methods demonstrate excellent green fluorescent protein (GFP) expression after suprachoroidal injection of PBAE nanoparticles containing a CMV-GFP expression plasmid.

As shown in FIG. 3, Brown Norway rats were given suprachoroidal injection of 3 μL of PBS or a suspension of PBAE nanoparticles containing 1 μg of a CMV-GFP expression plasmid in one eye. After two months, ocular frozen sections were immunostained for GFP (red) and counterstained with DAPI. A section close to the site of suprachoroidal injection in a control rat shows no GFP staining (FIG. 3, upper left), i.e., there is no expression of GFP in retinas of control eyes, while a section near the site of suprachoroidal injection of CMV-GFP nanoparticles shows strong staining for GFP in photoreceptor inner and outer segments and lighter staining in some inner retinal cells two months after suprachoroidal injection of 3 μL of nanoparticle suspension containing 1 μg of CMV-GFP expression plasmid. An ocular section near the site of suprachoroidal injection shows strong GFP immunostaining in photoreceptor inner and outer segments and lighter staining in some inner retinal cells (FIG. 3, top right).

In the same eye, a section through posterior retina remote from the site of CMV-GFP nanoparticle injection shows strong GFP staining in photoreceptor inner and outer segments, and inner retinal neurons, with some light staining in the choroid that is best seen when there is no counterstaining (FIG. 3, bottom left, no counterstain). Counterstaining of nuclei with DAPI provides orientation (FIG. 3, bottom right).

Referring now to FIG. 4, Brown Norway rats were given a suprachoroidal injection of a suspension of PBAE nanoparticles containing 1 μg of a CMV-GFP expression plasmid in one eye. Two or four weeks after injection, GFP mRNA was measured in the retina and RPE/choroid by real time quantitative PCR. Each bar represents the mean (±SEM) level of mRNA for GFP. The mean level of mRNA for GFP was significantly greater in RPE/choroid compared with retina at both 2 and 4 weeks after injection, and expression in each tissue was not significantly changed between 2 and 4 weeks. These results demonstrate that expression of mRNA for GFP is greater in RPE/choroid than in retina after suprachoroidal injection of CMV-GFP nanoparticles, and there is no decline in expression in both tissues between 2 and 4 weeks (FIG. 4).

As shown in FIG. 5, the level of GFP protein in the retina and RPE/choroid was measured by ELISA at several time points after suprachoroidal injection of nanoparticles containing 1 μg of CMV-GFP expression plasmid. Brown Norway rats were given suprachoroidal injection of a suspension of PBAE nanoparticles containing 1 μg of a CMV-GFP expression plasmid in both eyes. At 1, 2, 4, 8, or 16 weeks after injection, rats were euthanized, eyes were removed, retinas were dissected and retinas and eyecups containing RPE, choroid, and sclera were homogenized in ELISA buffer, and an ELISA evaluating for GFP was performed. Bars show the mean (±SEM) level of GFP at each time point. The levels of GFP protein peaked at 4 weeks after injection and were significantly greater in RPE/choroid compared with retina (FIG. 5). GFP protein was still detectable at 16 weeks after injection, the longest time point measured.

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Campochiaro P A, Lauer A K, Sohn E H, et al., Lentiviral vector gene transfer of endostatin/angiostatin for macular degeneration (GEM) study. Hum Gene Ther 2016; 28(1): 99-111.

Vandenberghe L H, Bell P, Maguire A M, et al., Dosage thresholds for AAV2 and AAV8 photoreceptor gene therapy in monkey. Sci Trans Med 2011; 3(88):1-9.

Heier J S, Kherani S, Desai S, et al., Intravitreous injection of AAV2-sFLT01 in patients with advanced neovascular age-related macular degeneration: a phase 1, open-label trial. The Lancet 2017; 389:May 17. pii: S0140-6736(17) 30979-0. doi: 10.1016/S0140-6736(17)-0. [Epub ahead of print].

Li Q, Miller R, Han P Y, et al., Intraocular route of administration defines humoral immune response and therapeutic potential. Mol Ther 2008; 14:1760-9.

Kotterman M A, Yin L, Strazzeri J M, et al., Antibody neutralization poses a barrier to intravitreal adeno-associated viral vector gene delivery to non-human primates. Gene Ther 2014; 22(12):116-26.

Patel S R, P. LAS, Edelhauser H F, Prausnitz M R, Suprachoroidal drug delivery to the back of the eye using hollow needles. Pharm Res 2011; 28(1):166-76.

Patel S R, Berezovsky D E, McCarey B E, et al., Targeted administration into the suprachoroidal space using a microneedle for drug delivery to the posterior segment of the eye. Invest Ophthalmol Vis Sci 2012; 53(8):4433-41.

Green J J, Langer R, Anderson D G, A combinatorial polymer library approach yields insight into nonviral gene delivery. Acc Chem Res 2008 May 29; 41(6):749-759. Acc Chem Res 2008; 41:749-59.

Sunshine J C, Green J J, Mahon K P, et al., Small molecule end-groups of linerar polymer determine cell-type delivery efficacy. Adv Mater 2009; 21:4947-51.

Sunshine J C, Sunshine S B, Bhutto I, et al., Poly(B-amino ester)-nanoparticle mediated transfection of retinal pigmented epithelial cells in vitro and in vivo. PLoS One 2012; 7:e37453.

Guerrero-Cazares H, Tzeng S Y, Young N P, et al., Biodegradable polymeric nanoparticles show high efficacy and specificity at DNA delivery to human glioblastoma in vitro and in vivo. ACS Nano 2014; 8(5):5141-53.

Mangraviti A, Tzeng S Y, Kozielski K L, et al., Polymeric nanoparticles for nonviral gene therapy extend brain tumor survival in vivo. ACS Nano 2015; 9(2):1236-49.

Campochiaro P A, Aiello L P, Rosenfeld P J, Anti-vascular endothelial growth factor agents in the treatment of retinal disease. From bench to bedside. Ophthalmology 2016; 123 (10S):S78-S88.

Shen J, Frye M, Lee B L, et al., Targeting VE-PTP activates TIE2 and stabilizes the ocular vasculature. J Clin Invest 2014; 124(10):4564-76.

Campochiaro P A, Khanani A, Singer M, et al., Enhanced benefit in diabetic macular edema from AKB-9778 Tie2 activation combined with vascular endothelial growth factor suppression. Ophthalmology 2016; 123(8):1722-30.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating a disease or condition of the eye, the method comprising non-virally transfecting one or more cells in a suprachoroidal space by administering to a suprachoroidal space of an eye of a subject a composition comprising a nanoparticle or a microparticle comprising a poly(beta-amino ester) (PBAE) and a therapeutic agent, wherein the therapeutic agent is selected from an expression construct, a therapeutic transgene, a therapeutic protein, a viral vector, a plasmid, a gene, a nucleic acid, DNA, RNA, and mRNA, and wherein the PBAE is $$R''{-}NH{-}\underset{}{\overset{O}{\|}}{-}R{-}\left[\underset{R_5\ R_4\ R'\ R_3\ R_2}{\overset{O\ \ R_9\ R_8\ R_7\ R_6\ \ O}{\|\ \ \ \ \ \ \ \ \ \ \ \ \ \ \|}}{-}R{-}\right]_n{-}\underset{}{\overset{O}{\|}}{-}NH{-}R'' \quad (I)$$

wherein:

n is an integer from 1 to 10,000;

$R_1$, $R_2$, $R_3$, $R_4$, $R_5$, $R_6$, $R_7$, $R_8$, and $R_9$ are each hydrogen;

$R_1$ is absent and when present the compound of formula (I) further comprises a counter ion selected from the group consisting of chloride, fluoride, bromide, iodide, sulfate, nitrate, fumarate, acetate, carbonate, stearate, laurate, and oleate; and R is (B4) $\text{—O—(CH}_2)_4\text{—O—}$ ;

R' is (S4) $\text{—(CH}_2)_4\text{—OH}$ or (S5) $\text{—(CH}_2)_6\text{—OH}$; and R'' is (E7) $\text{—(CH}_2)_3\text{—N(piperazine)—CH}_3$.

2. The method of claim 1, wherein the nanoparticle or the microparticle is formulated to spread after delivery to the suprachoroidal space and uniformly distribute and localize in a region of the suprachoroidal space.

3. The method of claim 1, wherein the composition further comprises a pharmaceutically acceptable carrier.

4. The method of claim 1, wherein the therapeutic agent neutralizes or stimulates the activity of a protein in the eye, neutralizes the activity of a growth factor, or stimulates the activity of a growth factor.

5. The method of claim 4, wherein the therapeutic agent neutralizes or stimulates the activity of at least one of vascular endothelial growth factor (VEGF), platelet-derived growth factor (PDGF), angiopoietin 2 (Angpt2), vascular endothelial-protein tyrosine phosphate (VE-PTP), or combinations thereof.

6. The method of claim 1, wherein the nanoparticle or the microparticle localizes to at least one specific cell type in the eye.

7. The method of claim 6, wherein the at least one cell type is a retinal ganglion cell, amacrine cell, Müller cell, astrocyte, photoreceptor cell, cone cell, rod cell, bipolar cell, horizontal cell, retinal pigment epithelial cell, choroidal cell, and/or a scleral cell.

8. The method of claim 1, wherein the disease or condition is selected from the group consisting of age-related macular degeneration (AMD), neovascular age-related macular degeneration (NVAMD), retinitis pigmentosa (RP), optic neuritis, infection, uveitis, sarcoid, sickle cell disease, retinal detachment, temporal arteritis, retinal ischemia, choroidal ischemia, choroidal ischemia, ischemic optic neuropathy, arteriosclerotic retinopathy, hypertensive retinopathy, retinal artery blockage, retinal vein blockage, glaucoma, hypotension, diabetic retinopathy, diabetic macular edema (DME), macular edema occurring after retinal vein occlusion (RVO), macular edema, and choroidal neovascularization.

9. The method of claim 1, wherein the disease or condition is an inherited retinal degeneration.

10. The method of claim 1, wherein the therapeutic agent comprises a gene associated with inherited retinal degeneration.

11. The method of claim 10, wherein the nanoparticle or microparticle encapsulates a plasmid that encodes a gene that replaces defective genes due to inherited retinal diseases, wherein the gene is selected from the group consisting of RPE65, BEST1, NR2E3, NRL, RHO, RP1, an autosomal dominant, an autosomal recessive gene, and an X-linked gene.

12. The method of claim 11, wherein the X-linked gene is selected from the group consisting of RPGR, RP2, and OFD1.

13. The method of claim 9, wherein the disease or condition is selected from the group consisting of Stargardt disease, choroideremia, achromatopsia, and X-linked retinitis pigmentosa.

14. The method of claim 9, wherein the disease or condition includes cone cell death in a subject afflicted with retinitis pigmentosa.

15. The method of claim 1, wherein the therapeutic agent comprises a therapeutic protein for preventing cone cell death in a subject afflicted with retinitis pigmentosa.

16. The method of claim 15, wherein the nanoparticle or microparticle encapsulates a plasmid that encodes NRF2, GDNF, or another gene that is neuroprotective to the retina.

17. The method of claim 1, wherein the composition is administered at least twice, and wherein each administration is done at a different time point.

18. The method of claim 1, wherein the composition is administered at a dosage of about 0.0001 mg/kg to about 5 mg/kg.

* * * * *